United States Patent
Dassau et al.

(10) Patent No.: US 12,128,212 B2
(45) Date of Patent: Oct. 29, 2024

(54) ADAPTIVE ZONE MODEL PREDICTIVE CONTROL WITH A GLUCOSE AND VELOCITY DEPENDENT DYNAMIC COST FUNCTION FOR AN ARTIFICIAL PANCREAS

(71) Applicant: PRESIDENT AND FELLOWS OF HARVARD COLLEGE, Cambridge, MA (US)

(72) Inventors: Eyal Dassau, Cambridge, MA (US); Francis J. Doyle, III, Cambridge, MA (US); Dawei Shi, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 899 days.

(21) Appl. No.: 16/973,628

(22) PCT Filed: Jun. 19, 2019

(86) PCT No.: PCT/US2019/037923
§ 371 (c)(1),
(2) Date: Dec. 9, 2020

(87) PCT Pub. No.: WO2019/246213
PCT Pub. Date: Dec. 26, 2019

(65) Prior Publication Data
US 2021/0162127 A1     Jun. 3, 2021

Related U.S. Application Data

(60) Provisional application No. 62/686,931, filed on Jun. 19, 2018.

(51) Int. Cl.
*A61M 5/172* (2006.01)
*G16H 10/60* (2018.01)
(Continued)

(52) U.S. Cl.
CPC .......... *A61M 5/1723* (2013.01); *G16H 10/60* (2018.01); *G16H 20/17* (2018.01); *G16H 40/40* (2018.01);
(Continued)

(58) Field of Classification Search
CPC ...... A61M 5/1723; A61M 2005/14208; A61M 2230/201; A61M 2202/0486;
(Continued)

(56) References Cited

U.S. PATENT DOCUMENTS

| 5,707,641 A | 1/1998 | Gertner et al. |
| 5,746,697 A | 5/1998 | Swedlow et al. |

(Continued)

FOREIGN PATENT DOCUMENTS

WO     2018009614 A1     1/2018

OTHER PUBLICATIONS

Abrahamsson et al. "Gastric bypass reduces symptoms and hormonal responses in hypoglycemia." Diabetes 65(9): 2667-2675 (2016).

(Continued)

*Primary Examiner* — Rami R Okasha
(74) *Attorney, Agent, or Firm* — NIXON PEABODY LLP; David S. Resnick; Wayne Tang

(57) ABSTRACT

A system for the delivery of insulin to a patient is provided. The systems and methods disclose include an insulin delivery device configured to deliver insulin to a patient in response to control signals. The system also includes a controller programmed to receive the sensor glucose measurement signal from the glucose sensor. The sensor glucose measurement signal received indicates a concentration of the real time glucose concentration in a bloodstream. The controller is further configured to enact an impeding glycemia protocol based on a zone model predictive control (MPC)

(Continued)

algorithm in response to the real time glucose concentration. The impeding glycemia protocol includes in determining a relationship between predicted glucose concentrations, a rate of change of the predicted glucose concentrations, and a set of control parameters that determine insulin doses above and below a patient-specific basal rate.

14 Claims, 7 Drawing Sheets

(51) Int. Cl.
    *G16H 20/17*     (2018.01)
    *G16H 40/40*     (2018.01)
    *G16H 40/67*     (2018.01)
    *G16H 50/20*     (2018.01)
    *G16H 50/30*     (2018.01)
    *G16H 70/40*     (2018.01)
    *A61M 5/142*     (2006.01)

(52) U.S. Cl.
    CPC .............. *G16H 40/67* (2018.01); *G16H 50/20* (2018.01); *G16H 50/30* (2018.01); *G16H 70/40* (2018.01); *A61M 2005/14208* (2013.01); *A61M 2230/201* (2013.01)

(58) Field of Classification Search
    CPC ....... A61M 5/142; G16H 10/60; G16H 20/17; G16H 40/40; G16H 40/67; G16H 50/20; G16H 50/30; G16H 70/40
    See application file for complete search history.

(56) References Cited

U.S. PATENT DOCUMENTS

| | | | |
|---|---|---|---|
| 10,117,992 B2 | 11/2018 | Parikh et al. | |
| 10,546,659 B2 | 1/2020 | Kovatchev et al. | |
| 2004/0122353 A1 | 6/2004 | Shahmirian et al. | |
| 2004/0158232 A1 | 8/2004 | Schetky et al. | |
| 2005/0044436 A1 | 2/2005 | Holle | |
| 2005/0272640 A1 | 12/2005 | Doyle et al. | |
| 2007/0016127 A1 | 1/2007 | Staib et al. | |
| 2007/0244575 A1 | 10/2007 | Wojsznis et al. | |
| 2007/0276512 A1 | 11/2007 | Fan et al. | |
| 2008/0033271 A1 | 2/2008 | Say et al. | |
| 2008/0208113 A1 | 8/2008 | Damiano et al. | |
| 2008/0235053 A1 | 9/2008 | Ray et al. | |
| 2009/0143725 A1 | 6/2009 | Peyser et al. | |
| 2009/0315772 A1 | 12/2009 | Wengler et al. | |
| 2010/0198142 A1 | 8/2010 | Sloan et al. | |
| 2010/0262117 A1 | 10/2010 | Magni et al. | |
| 2010/0280441 A1 | 11/2010 | Wilinska et al. | |
| 2010/0298685 A1 | 11/2010 | Hayter et al. | |
| 2011/0098548 A1 | 4/2011 | Budiman et al. | |
| 2011/0106011 A1 | 5/2011 | Cinar et al. | |
| 2011/0208156 A1 | 8/2011 | Doyle et al. | |
| 2013/0018232 A1 | 1/2013 | D'Souza et al. | |
| 2014/0005633 A1 | 1/2014 | Finan | |
| 2014/0081236 A1 | 3/2014 | Wilinska et al. | |
| 2014/0121488 A1 | 5/2014 | Budiman | |
| 2014/0180240 A1 | 6/2014 | Finan et al. | |
| 2014/0200559 A1 | 7/2014 | Doyle et al. | |
| 2014/0276554 A1 | 9/2014 | Finan et al. | |
| 2014/0276555 A1 | 9/2014 | Morales | |
| 2014/0379273 A1 | 12/2014 | Petisce et al. | |
| 2015/0100038 A1* | 4/2015 | McCann ............. | A61M 5/1723 604/504 |
| 2015/0134356 A1 | 5/2015 | Atlas et al. | |
| 2015/0309486 A1 | 10/2015 | Webersinke et al. | |
| 2016/0030670 A1 | 2/2016 | Fischl | |
| 2016/0038673 A1 | 2/2016 | Morales | |
| 2016/0048119 A1 | 2/2016 | Wojsznis et al. | |
| 2016/0163037 A1 | 6/2016 | Dehais et al. | |
| 2016/0170384 A1 | 6/2016 | Charest-Finn et al. | |
| 2016/0281489 A1 | 9/2016 | Dykstra et al. | |
| 2017/0000943 A1 | 1/2017 | Blomquist et al. | |
| 2017/0017212 A1 | 1/2017 | Collins et al. | |
| 2017/0099011 A1 | 4/2017 | Freeman et al. | |
| 2017/0136160 A1 | 5/2017 | Barral et al. | |
| 2017/0143899 A1* | 5/2017 | Gondhalekar ........ | A61M 5/142 |
| 2017/0173262 A1 | 6/2017 | Veltz | |
| 2017/0192400 A1 | 7/2017 | Hofschulz et al. | |
| 2017/0216518 A1 | 8/2017 | Davis et al. | |
| 2017/0249445 A1 | 8/2017 | Devries et al. | |
| 2018/0147349 A1 | 5/2018 | Finan et al. | |
| 2018/0271418 A1 | 9/2018 | Hayter et al. | |
| 2018/0353112 A1 | 12/2018 | Dassau et al. | |
| 2018/0369479 A1 | 12/2018 | Hayter et al. | |
| 2019/0192768 A1 | 6/2019 | Gupta et al. | |
| 2019/0244713 A1 | 8/2019 | Warren | |
| 2020/0268968 A1 | 8/2020 | Steil et al. | |

OTHER PUBLICATIONS

American Diabetes Association. "2. Classification and diagnosis of diabetes: standards of medical care in diabetes." Diabetes care 41(1): S13-S27 (2018).

American Diabetes Association. "8. Pharmacologic approaches to glycemic treatment: standards of medical care in diabetes-2018." Diabetes care 41(1): S73-S85 (2018).

Andersen et al. "Interior-point methods for large-scale cone programming." Optimization for machine learning 5583: 56-83 (2011).

Banerjee et al. "Model based safety analysis and verification of cyber-physical systems" Dissertation, Arizona State University (2012).

Bansal et al. "Goal-driven dynamics learning via Bayesian optimization." 2017 IEEE 56th Annual Conference on Decision and Control (CDC). IEEE, 5168-5173 (2017).

Beck et al. "Frequency of morning ketosis after overnight insulin suspension using an automated nocturnal predictive low glucose suspend system." Diabetes Care 37(5): 1224-1229 (2014).

Bell et al. "Impact of fat, protein, and glycemic index on postprandial glucose control in type 1 diabetes: implications for intensive diabetes management in the continuous glucose monitoring era." Diabetes care 38(6): 1008-1015 (2015).

Bemporad et al. "The explicit linear quadratic regulator for constrained systems." Automatica 38(1): 3-20 (2002).

Benosman et al. "Bayesian optimization-based modular indirect adaptive control for a class of nonlinear systems." IFAC-PapersOnLine 49(13): 253-258 (2016).

Bergenstal et al. "Safety of a hybrid closed-loop insulin delivery system in patients with type 1 diabetes." Jama 316(13): 1407-1408 (2016).

Bernardini et al. "Energy-aware robust model predictive control based on noisy wireless sensors." Automatica 48(1): 36-44 (2012).

Blauw et al. "Performance and safety of an integrated bihormonal artificial pancreas for fully automated glucose control at home." Diabetes, Obesity and Metabolism 18(7): 671-677 (2016).

Breton et al. "Fully integrated artificial pancreas in type 1 diabetes: modular closed-loop glucose control maintains near normoglycemia." Diabetes 61(9): 2230-2237 (2012).

Bristow et al. "A survey of iterative learning control." IEEE control systems magazine 26(3): 96-114 (2006).

Burnett et al. "Glucose sensing in the peritoneal space offers faster kinetics than sensing in the subcutaneous space." Diabetes 63(7): 2498-2505 (2014).

Cameron et al., "A closed-loop artificial pancreas based on risk management." Journal of diabetes science and technology 5(2): 368-379 (2011).

Cameron et al. "Extended multiple model prediction with application to blood glucose regulation," J. Process Control 22(8): 1422-1432 (2012).

Campos-Cornjeo et al. "An advisory protocol for rapid-and slow-acting insulin therapy based on a run-to-run methodology." Diabetes Technology & Therapeutics 12.7 (2010): 555-565.

Campos-Cornejo et al. "Adaptive control algorithm for a rapid and slow acting insulin therapy following run-to-run methodology." Proceedings of the 2010 American Control Conference. IEEE (2010).

(56) References Cited

OTHER PUBLICATIONS

Campos-Delgado et al. "Self-tuning insulin adjustment algorithm for type 1 diabetic patients based on multi-doses regime." Applied Bionics and Biomechanics 2(2): 61-71 (2005).

Campos-Delgado et al. "Fuzzy-based controller for glucose regulation in type-1 diabetic patients by subcutaneous route." IEEE Transactions on Biomedical Engineering 53(11): 2201-2210 (2006).

Carrasco et al. "Design of MDIs for type 1 diabetes treatment via rolling horizon cardinality-constrained optimisation." IFAC—PapersOnLine 50(1): 15044-15049 (2017).

Castle et al. "Comparative pharmacokinetic/pharmacodynamic study of liquid stable glucagon versus lyophilized glucagon in type 1 diabetes subjects." Journal of diabetes science and technology 10(5): 1101-1107 (2016).

Ceriello et al. "Postprandial glucose regulation and diabetic complications." Archives of internal medicine 164(19): 2090-2095 (2004).

Cescon et al. "Impulsive predictive control of T1DM glycemia: an in-silico study." Dynamic Systems and Control Conference. American Society of Mechanical Engineers vol. (45295): 319-326 (2012).

Chakrabarty et al. "Support vector machine informed explicit nonlinear model predictive control using low-discrepancy sequences." IEEE Transactions on Automatic Control 62(1): 135-148 (2016).

Chakrabarty et al. "Event-triggered model predictive control for embedded artificial pancreas systems." IEEE Transactions on Biomedical Engineering 65(3): 575-586 (2017).

Charest et al., "MPC enhancement for tracking of complex profiles—The basic technique." Control Engineering Practice 33: 136-147 (2014).

Cherrington et al. "The role of insulin and glucagon in the regulation of basal glucose production in the postabsorptive dog." The Journal of clinical investigation 58(6): 1407-1418 (1976).

Cherrington. "Control of glucose uptake and release by the liver in vivo." Diabetes 48(5): 1198-1214 (1999).

Cinar. "Artificial pancreas systems: an introduction to the special issue." IEEE Control Systems Magazine 38(1): 26-29 (2018).

Clark et al. "Even silent hypoglycemia induces cardiac arrhythmias." Diabetes 63(5): 1457-1459 (2014).

Colberg et al. "Pumping insulin during exercise: What healthcare providers and diabetic patients need to know." The physician and sportsmedicine 30(4): 33-38 (2002).

Colmegna et al. "Switched LPV glucose control in type 1 diabetes." IEEE Transactions on Biomedical Engineering 63(6): 1192-1200 (2016).

"Dalla-Man et al. ""GIM, simulation software of meal glucose-insulin model."" Journal of Diabetes Science and Technology 1(3): 323-330 (2007)".

Dalla-Man et al. "Meal simulation model of the glucose-insulin system." IEEE Transactions on biomedical engineering 54(10): 1740-1749 (2007).

Dalla-Man et al. "The UVA/PADOVA type 1 diabetes simulator: new features." Journal of diabetes science and technology 8(1): 26-34 (2014).

Dassau et al. "Modular artificial β-cell system: a prototype for clinical research." Journal of Diabetes Science and Technology 2(5): 863-872 (2008).

Dassau et al. "In silico evaluation platform for artificial pancreatic β-cell development—a dynamic simulator for closed-loop control with hardware-in-the-loop." Diabetes technology & therapeutics 11(3): 187-194 (2009).

Dassau et al. "Real-time hypoglycemia prediction suite using continuous glucose monitoring: a safety net for the artificial pancreas." Diabetes care 33(6): 1249-1254 (2010).

Dassau et al. "Intraperitoneal insulin delivery provides superior glycaemic regulation to subcutaneous insulin delivery in model predictive control-based fully-automated artificial pancreas in patients with type 1 diabetes: a pilot study." Diabetes, Obesity and Metabolism 19(12): 1698-1705 (2017).

Dassau et al. "Twelve-week 24/7 ambulatory artificial pancreas with weekly adaptation of insulin delivery settings: effect on hemoglobin A1c and hypoglycemia." Diabetes Care 40(12): 1719-1726 (2017).

Davidson et al. "Analysis of guidelines for basal-bolus insulin dosing: basal insulin, correction factor, and carbohydrate-to-insulin ratio." Endocrine Practice 14(9): 1095-1101 (2008).

Del Prato et al. "Effect of sustained physiologic hyperinsulinaemia and hyperglycemia on insulin secretion and insulin sensitivity in man." Diabetologia 37(10): 1025-1035 (1994).

Dobbins et al. "Compartmental modeling of glucagon kinetics in the conscious dog." Metabolism 44(4): 452-459 (1995).

Domanski et al., "Assessment of predictive control performance using fractal measures." Nonlinear Dynamics 89(2): 773-790 (2017).

Doyle III et al. "Closed-loop artificial pancreas systems: engineering the algorithms." Diabetes care 37(5): 1191-1197 (2014).

Duivenvoorden et al. "Constrained Bayesian optimization with particle swarms for safe adaptive controller tuning." IFAC—PapersOnLine 50(1): 11800-11807 (2017).

Eaton et al. "Hepatic removal of insulin in normal man: dose response to endogenous insulin secretion." The Journal of Clinical Endocrinology & Metabolism 56(6): 1294-1300 (1983).

Craig et al. "Critical role for GLP-1 in symptomatic post-bariatric hypoglycaemia." Diabetologia 60(3): 531-540 (2017).

Dassau et al. "Adjustment of open-loop settings to improve closed-loop results in type 1 diabetes: a multicenter randomized trial." The Journal of Clinical Endocrinology & Metabolism 100(10): 3878-3886 (2015).

Halperin et al. "Continuous glucose monitoring for evaluation of glycemic excursions after gastric bypass." Journal of Obesity, vol. 2011, Article ID 869536, 7 pages (2011).

Halperin et al. "Glucagon treatment for post-gastric bypass hypoglycemia." Obesity 18(9): 1858-1860 (2010).

Harvey et al. "Clinical evaluation of an automated artificial pancreas using zone-model predictive control and health monitoring system." Diabetes technology & therapeutics 16(6): 348-357 (2014).

Harvey et al. "Design of the health monitoring system for the artificial pancreas: low glucose prediction module." Journal of diabetes science and technology 6(6): 1345-1354 (2012).

Haymond et al. "Nonaqueous, mini-dose glucagon for treatment of mild hypoglycemia in adults with type 1 diabetes: a dose-seeking study." Diabetes Care 39(3): 465-468 (2016).

Suhl et al. "Medical nutrition therapy for post-bariatric hypoglycemia: practical insights." Surgery for Obesity and 8 Related Diseases 13(5): 888-896 (2017).

Reddy et al. "Metabolic control with the bio-inspired artificial pancreas in adults with type 1 diabetes: a 24-hour randomized controlled crossover study." Journal of diabetes science and technology 10(2): 405-413 (2016).

Renard et al. "Complications of the pump pocket may represent a significant cause of incidents with implanted systems for intraperitoneal insulin delivery." Diabetes Care 17(9): 1064-1066 (1994).

Renard et al. "Insulin underdelivery from implanted pumps using peritoneal route: determinant role of insulin pump compatibility." Diabetes Care 19(8): 812-817 (1996).

Renard et al. "Artificial β-cell: clinical experience toward an implantable closed-loop insulin delivery system." Diabetes & metabolism 32(5): 497-502 (2006).

Renard et al. "Closed-loop insulin delivery using a subcutaneous glucose sensor and intraperitoneal insulin delivery: feasibility study testing a new model for the artificial pancreas." Diabetes care 33(1): 121-127 (2010).

Renard et al. "Lower rate of initial failures and reduced occurrence of adverse events with a new catheter model for continuous subcutaneous insulin infusion: prospective, two-period, observational, multicenter study." Diabetes technology & therapeutics 12(10): 769-773 (2010).

Reubi et al. "Distribution of somatostatin receptors in normal and tumor tissue." Metabolism 39(9): 78-81 (1990).

Richter et al. "Computational complexity certification for real-time MPC with input constraints based on the fast gradient method." IEEE Transactions on Automatic Control 57(6): 1391-1403 (2012).

Rivera et al., "Internal model control: PID controller design." Ind. Eng. Chem. Process Des. Dev. 25: 252-265 (1986).

(56) References Cited

OTHER PUBLICATIONS

Rohlfing et al. "Defining the relationship between plasma glucose and HbA1c: analysis of glucose profiles and HbA1c in the Diabetes Control and Complications Trial." Diabetes care 25(2): 275-278 (2002).
Ruiz et al. "Effect of insulin feedback on closed-loop glucose control: a crossover study." Journal of diabetes science and technology 6(5):1123-1130 (2012).
Russell et al. "Day and night glycaemic control with a bionic pancreas versus conventional insulin pump therapy in preadolescent children with type 1 diabetes: a randomised crossover trial." The lancet Diabetes & endocrinology 4(3): 233-243 (2016).
Salehi et al. "Blockade of glucagon-like peptide 1 receptor corrects postprandial hypoglycemia after gastric bypass." Gastroenterology 146(3): 669-680 (2014).
Salehi et al. "Altered islet function and insulin clearance cause hyperinsulinemia in gastric bypass patients with symptoms of postprandial hypoglycemia." The Journal of Clinical Endocrinology & Metabolism 99(6): 2008-2017 (2014).
Sanz et al. "Design and clinical evaluation of a novel low-glucose prediction algorithm with mini-dose stable glucagon delivery in post-bariatric hypoglycemia." Diabetes technology & therapeutics 20(2): 127-139 (2018).
Sarwar et al. "Hypoglycemia after Roux-en-Y gastric bypass: the BOLD experience." Obesity surgery 24(7): 1120-1124 (2014).
Scavini et al. "Intraperitoneal Insulin Absorption After Lona-Term Intraperitoneal Insulin Therapy." Diabetes care 18(1): 56-59 (1995).
Schaepelynck et al. "A recent survey confirms the efficacy and the safety of implanted insulin pumps during long-term use in poorly controlled type 1 diabetes patients." Diabetes technology & therapeutics 13(6): 657-660 (2011).
Schauer et al. "Bariatric surgery versus intensive medical therapy for diabetes—3-year outcomes." New England Journal of Medicine 370(21): 2002-2013 (2014).
Schmelzeisen-Redeker et al. "Time delay of CGM sensors: relevance, causes, and countermeasures." Journal of diabetes science and technology 9(5): 1006-1015 (2015).
Seborg et al., "Chapter 20, Model Predictive Control", Process Dynamics and Control: 414-438 (2011).
Seita et al. "Development of canine models of type 1 diabetes with partial pancreatectomy and the administration of streptozotocin." Cell Medicine 6.(1-2): 25-31 (2013).
Shahriari et al. "Taking the human out of the loop: A review of Bayesian optimization." Proceedings of the IEEE 104(1): 148-175 (2015).
Shapiro et al. "An analysis of variance test for normality (complete samples)." Biometrika 52(3/4): 591-611 (1965).
Soon-Shiong et al. "Successful reversal of spontaneous diabetes in dogs by intraperitoneal microencapsulated islets." Transplantation 54(5): 769-774 (1992).
Soru et al., "MPC based artificial pancreas: strategies for individualization and meal compensation." Annual Reviews in Control 36.1 (2012): 118-128.
Spaan et al. "Implantable insulin pumps: an effective option with restricted dissemination." The Lancet Diabetes & Endocrinology 2(5): 358-360 (2014).
Steil et al. "Automated insulin delivery for type 1 diabetes." Current Opinion in Endocrinology, Diabetes and Obesity 13(2): 205-211 (2006).
Steil et al. "Feasibility of automating insulin delivery for the treatment of type 1 diabetes." Diabetes 55(12): 3344-3350 (2006).
Szücs et al. "A memory-efficient representation of explicit MPC solutions." 2011 50th IEEE Conference on Decision and Control and European Control Conference. IEEE. 1916-1921 (2011).
Tarin et al. "Comprehensive pharmacokinetic model of insulin glargine and other insulin formulations." IEEE Transactions on Biomedical Engineering 52(12): 1994-2005 (2005).
Tauschmann et al. "Day-and-night hybrid closed-loop insulin delivery in adolescents with type 1 diabetes: a free-living, randomized clinical trial." Diabetes Care 39(7): 1168-1174 (2016).
Thabit et al. "Home use of an artificial beta cell in type 1 diabetes." New England Journal of Medicine 373(22): 2129-2140 (2015).
Thabit et al. "Coming of age: the artificial pancreas for type 1 diabetes." Diabetologia 59(9): 1795-1805 (2016).
Toffanin et al. "Dynamic insulin on board: incorporation of circadian insulin sensitivity variation." Journal of diabetes science and technology 7(4): 928-940 (2013).
Toffanin et al. "Artificial pancreas: model predictive control design from clinical experience." Journal of Diabetes Science and Technology 7(6): 1470-1483 (2013).
Toffanin et al. "Toward a run-to-run adaptive artificial pancreas: In silico results." IEEE Transactions on Biomedical Engineering 65(3): 479-488 (2017).
Trimpe et al. "A self-tuning LQR approach demonstrated on an inverted pendulum." IFAC Proceedings vols. 47(3): 11281-11287 (2014).
Trogmann et al. "Hybrid control of type 1 diabetes bolus therapy." 49th IEEE Conference on Decision and Control (CDC). IEEE. 4721-4726 (2010).
Turksoy et al. "Multivariable adaptive identification and control for artificial pancreas systems." IEEE Transactions on Biomedical Engineering 61(3): 883-891 (2013).
Turksoy et al. "Adaptive control of artificial pancreas systems—a review." Journal of healthcare engineering 5(1): 1-22 (2014).
Turksoy et al. "An Integrated Multivariable Artificial Pancreas Control System", Journal of Diabetes Science and Tech 8(3): 498-507 (2014).
Tvarijonaviciute et al. "Obesity-related metabolic dysfunction in dogs: a comparison with human metabolic syndrome." BMC Veterinary Research 8(1): 1-8 (2012).
Tyagounov. "High-performance model predictive control for process industry." Technische Universiteit Eindhoven, Eindhoven, Netherlands (2004).
Valderas et al. "Acarbose improves hypoglycaemia following gastric bypass surgery without increasing glucagon-like peptide 1 levels." Obesity surgery 22(4): 582-586 (2012).
Van Bon et al. "Feasibility of a portable bihormonal closed-loop system to control glucose excursions at home under free-living conditions for 48 hours." Diabetes technology & therapeutics 16(3): 131-136 (2014).
Van Dijk et al. "Intraperitoneal insulin infusion: treatment option for type 1 diabetes resulting in beneficial endocrine effects beyond glycaemia." Clinical endocrinology 81(4): 488-497 (2014).
Van Dijk et al. "Continuous intraperitoneal insulin infusion versus subcutaneous insulin therapy in the treatment of type 1 diabetes: effects on glycemic variability." Diabetes technology & therapeutics 17(6): 379-384 (2015).
Van Dijk et al. "Different effects of intraperitoneal and subcutaneous insulin administration on the GH-IGF-1 axis in type 1 diabetes." The Journal of Clinical Endocrinology & Metabolism 101(6): 2493-2501 (2016).
Van Heusden et al., "Control-Relevant Models for Glucose Control Using a priori patient characteristics." IEEE transactions on biomedical engineering 59(7): 1839-1849 (2011).
Gondhalekar et al., "Velocity-weighting & velocity-penalty MPC of an artificial pancreas: Improved safety & performance", Automatica 91, 105-117, (2018).
Gondhalekar et al., "MPC Design for Rapid Pump-Attenuation and Expedited Hyperglycemia Response to Treat T1DM with an Artificial Pancreas", Proc. Am. Control Conf., 4224-4230, (2014).
Shi et al., "Adaptive Zone Model Predictive Control of Artificial Pancreas Based on Glucose-and Velocity-Dependent Control Penalties", IEEE Transactions on Biomedical Engineering, 66, (4.), (2019).
International Search Report, PCT/US2019/037923, Apr. 9, 2019.
Edgerton et al. "Small increases in insulin inhibit hepatic glucose production solely caused by an effect on glycogen metabolism." Diabetes 50(8): 1872-1882 (2001).
El-Khatib et al. "Adaptive closed-loop control provides blood-glucose regulation using dual subcutaneous insulin and glucagon infusion in diabetic swine." Journal of Diabetes Science and Technology 1(2): 181-192 (2007).

(56) References Cited

OTHER PUBLICATIONS

Ellingsen et al. "Safety constraints in an artificial pancreatic β cell: an implementation of model predictive control with insulin on board." Journal of diabetes science and technology 3(3): 536-544 (2009).
Enso "Model Predictive Control and State Estimation", 1-112 (2013).
Eqtami et al. "Event-triggered control for discrete-time systems." Proceedings of the 2010 american control conference. IEEE. 4719-4724 (2010).
Eqtami et al. "Novel event-triggered strategies for model predictive controllers." 2011 50th IEEE Conference on Decision and Control and European Control Conference. IEEE. 1-7 (2011).
Eren-Oruklu et al. "Estimation of future glucose concentrations with subject-specific recursive linear models." Diabetes technology & therapeutics 11(4): 243-253 (2009).
Fernández-Esparrach et al. "Peroral endoscopic anastomotic reduction improves intractable dumping syndrome in Roux-en-Y gastric bypass patients." Surgery for Obesity and Related Diseases 6(1): 36-40 (2009).
Forlenza et al. "Application of zone model predictive control artificial pancreas during extended use of infusion set and sensor: a randomized crossover-controlled home-use trial." Diabetes Care 40(8): 1096-1102 (2017).
Fougner et al. "Intraperitoneal glucose sensing is sometimes surprisingly rapid." Modeling, Identification and Control 37(2): 121-131 (2016).
Fritsch et al. "Monotone piecewise cubic interpolation: algorithms and software." Siam J. Numer. Anal. 17(2): 238-246 (1980).
Garg et al. "Glucose outcomes with the in-home use of a hybrid closed-loop insulin delivery system in adolescents and adults with type 1 diabetes." Diabetes technology & therapeutics 19(3): 155-163 (2017).
"Gillis et al. ""Glucose estimation and prediction through meal responses using ambulatory subject data for advisory mode model predictive control."" Journal of Diabetes Science and Technology1(6): 825-833 (2007)".
Gin et al. "Combined improvements in implantable pump technology and insulin stability allow safe and effective long term intraperitoneal insulin delivery in type 1 diabetic patients: the EVADIAC experience." Diabetes & metabolism 29(6): 602-607 (2003).
Goldfine et al. "Patients with neuroglycopenia after gastric bypass surgery have exaggerated incretin and insulin secretory responses to a mixed meal." The Journal of Clinical Endocrinology & Metabolism 92(12): 4678-4685 (2007).
Goldfine et al. "How common is hypoglycemia after gastric bypass ?." Obesity (Silver Spring, Md.) 24(6): 1210-11 (2016).
Gondhalekar et al. "Periodic-zone model predictive control for diurnal closed-loop operation of an artificial pancreas." Journal of Diabetes Science and Technology 7(6): 1446-1460 (2013).
Gondhalekar et al. "Moving-horizon-like state estimation via continuous glucose monitor feedback in MPC of an artificial pancreas for type 1 diabetes." 53rd IEEE Conference on Decision and Control. IEEE. 310-315 (2014).
Gondhalekar et al. "Tackling problem nonlinearities & delays via asymmetric, state-dependent objective costs in MPC of an artificial pancreas." IFAC—PapersOnLine 48(23): 154-159 (2015).
Gondhalekar et al. "Periodic zone-MPC with asymmetric costs for outpatient-ready safety of an artificial pancreas to treat type 1 diabetes." Automatica 71: 237-246 (2016).
Gonzales et al., "Model predictive control tuning based on Extended Kalman Filter." 2017 IEEE Second Ecuador Technical Chapters Meeting (ETCM). IEEE, (2017).
Gonzalez et al., "A stable MPC with zone control", Journal of Process Control 19(1):110-122 (2009).
Gonzalez-Gonzalez et al. "Use of diazoxide in management of severe postprandial hypoglycemia in patient after Roux-en-Y gastric bypass." Surgery for Obesity and Related Diseases 9(1): e18-e19 (2013).

Goodyear et al. "Exercise, glucose transport, and insulin sensitivity." Annual review of medicine 49(1): 235-261 (1998).
Gregory et al. "Insulin delivery into the peripheral circulation: a key contributor to hypoglycemia in type 1 diabetes." Diabetes 64(10): 3439-3451 (2015).
Grosman et al., "Zone model predictive control: a strategy to minimize hyper-and hypoglycemic events" Journal of diabetes science and technology 4(4): 961-975 (2010).
Grosman et al. "Multi-zone-MPC: Clinical inspired control algorithm for the artificial pancreas." IFAC Proceedings vols. 44(A1161): 7120-7125 (2011).
Grosman et al. "Hybrid closed-loop insulin delivery in type 1 diabetes during supervised outpatient conditions." Journal of diabetes science and technology 10(3): 708-713 (2016).
Haidar. "The artificial pancreas: How closed-loop control is revolutionizing diabetes." IEEE Control Systems Magazine 36(5): 28-47 (2016).
Halperin et al. "Roux-en-Y gastric bypass surgery or lifestyle with intensive medical management in patients with type 2 diabetes: feasibility and 1-year results of a randomized clinical trial." JAMA surgery 149(7): 716-726 (2014).
Heemels et al. "An introduction to event-triggered and self-triggered control." 2012 IEEE 51st IEEE conference on decision and control (CDC). IEEE:1-16 (2012).
Heise et al. "Insulin stacking versus therapeutic accumulation: understanding the differences." Endocrine Practice 20(1): 75-83 (2014).
Hepburn et al. "Symptoms of acute insulin-induced hypoglycemia in humans with and without IDDM: factor-analysis approach." Diabetes Care 14(11): 949-957 (1991).
Horton. "Exercise and physical training: effects on insulin sensitivity and glucose metabolism." Diabetes/metabolism reviews 2(1-2): 1-17 (1986).
Horwitz et al. "Proinsulin, insulin, and C-peptide concentrations in human portal and peripheral blood." The Journal of clinical investigation 55(6): 1278-1283 (1975).
Hovorka et al. "Nonlinear model predictive control of glucose concentration in subjects with type 1 diabetes." Physiological measurement 25(4): 905-920 (2004).
Hovorka. "Continuous glucose monitoring and closed-loop systems." Diabetic medicine 23(1): 1-12 (2006).
HOW. "Special Issue on Artificial Pancreas Systems." IEEE Control Systems Magazine 38(1): 5-8 (2018).
Hu et al., "An improved PID algorithm based on insulin-on-board estimate for blood glucose control with Type 1 diabetes." Computational and Mathematical Methods in Medicine 2015(281589):1-9 (2015).
Huyett et al. "Design and evaluation of a robust PID controller for a fully implantable artificial pancreas." Industrial & engineering chemistry research 54(42): 10311-10321 (2015).
Huyett et al. "Preliminary evaluation of a long-term intraperitoneal glucose sensor with flushing mechanism." Journal of diabetes science and technology 10(5): 1192-1194 (2016).
Huyett et al. "Outpatient closed-loop control with unannounced moderate exercise in adolescents using zone model predictive control." Diabetes technology & therapeutics 19(6): 331-339 (2017).
Jost et al. "Optimal and suboptimal event-triggering in linear model predictive control." 2015 European Control Conference (ECC). IEEE 14: 1147-1152 (2015).
Kellogg et al. "Postgastric bypass hyperinsulinemic hypoglycemia syndrome: characterization and response to a modified diet." Surgery for Obesity and Related Diseases 4(4): 492-499 (2008).
Kefurt et al. "Hypoglycemia after Roux-En-Y gastric bypass: detection rates of continuous glucose monitoring (CGM) versus mixed meal test." Surgery for Obesity and Related Diseases 11(3): 564-569 (2015).
Kirchsteiger et al. "Robustness properties of optimal insulin bolus administrations for type 1 diabetes." American Control Conference. IEEE: 2284-2289 (2009).
Knab et al. "Zone model predictive control and moving horizon estimation for the regulation of blood glucose in critical care patients." IFAC—PapersOnLine 48(8): 1002-1007 (2015).

(56) References Cited

OTHER PUBLICATIONS

Visentin et al. "The UVA/Padova type 1 diabetes simulator goes from single meal to single day." Journal of diabetes science and technology 12(2): 273-281 (2018).

Vukmir et al. "Glucagon: prehospital therapy for hypoglycemia." Annals of emergency medicine 20(4): 375-379 (1991).

Wang et al. "Closed-loop control of artificial pancreatic beta-cell in type 1 diabetes mellitus using model predictive iterative learning control." IEEE Transactions on Biomedical Engineering 57(2): 211-219 (2009).

Wang et al. "Survey on iterative learning control, repetitive control, and run-to-run control." Journal of Process Control 19(10): 1589-1600 (2009).

Wang et al., "Automatic Bolus and Adaptive basal algorithm for the artificial pancreatic β-cell." Diabetes technology & therapeutics 12(11): 879-887 (2010).

Wang et al. ""Learning" can improve the blood glucose control performance for type 1 diabetes mellitus." Diabetes technology & therapeutics 19(1): 41-48 (2017).

Yeh et al. "Comparative effectiveness and safety of methods of insulin delivery and glucose monitoring for diabetes mellitus: a systematic review and meta-analysis." Annals of internal medicine 157(5): 336-347 (2012).

Yen et al. "Effect of somatostatin in patients with acromegaly: suppression of growth hormone, prolactin, insulin and glucose levels." New England Journal of Medicine 290(17): 935-938 (1974).

Zavitsanou et al. "Embedded control in wearable medical devices: Application to the artificial pancreas." Processes 4(35): 1-29 (2016).

Zisser et al. "Run-to-run control of meal-related insulin dosing." Diabetes technology & therapeutics 7(1): 48-57 (2005).

Zisser et al. "Clinical results of an automated artificial pancreas using technosphere inhaled insulin to mimic first-phase insulin secretion." Journal of diabetes science and technology 9(3): 564-572 (2015).

Li et al., An Ultra-low-power Medium Access Control Protocol for Body Sensor Network, Engineering in Medicine and Biology 27th Annual Conference 2451-2454 (2005).

McGraw-Hill Dictionary of Scientific & Technical Terms, 6E (Sep. 26, 2002) (2002).

Koerker et al. "Somatostatin: hypothalamic inhibitor of the endocrine pancreas." Science 184(4135): 482-484 (1974).

"Kovatchev et al. ""In silico preclinical trials: a proof of concept in closed-loop control of type 1 diabetes."" Journal of Diabetes Science and Technology3(1): 44-55 (2009)".

Kovatchev et al. "Safety of outpatient closed-loop control: first randomized crossover trials of a wearable artificial pancreas." Diabetes care 37(7): 1789-1796 (2014).

Kovatchev et al. "Feasibility of long-term closed-loop control: a multicenter 6-month trial of 24/7 automated insulin delivery." Diabetes technology & therapeutics 19(1): 18-24 (2017).

Lee et al., "A Closed-loop Artificial Pancreas based on the MPC: human friendly identification and automatic meal disturbance rejection." IFAC Proceedings 41(2): 4252-4257 (2008).

Lee et al. "Design and in silico evaluation of an intraperitoneal-subcutaneous (IP-SC) artificial pancreas." Computers & chemical engineering 70: 180-188 (2014).

Lee et al., "Enhanced model predictive control (eMPC) strategy for automated glucose control." Industrial & engineering chemistry research 55(46): 11857-11868 (2016).

Lehmann et al. "Event-triggered model predictive control of discrete-time linear systems subject to disturbances." 2013 European Control Conference (ECC). IEEE:1-6 (2013).

Liebl et al. "A reduction in severe hypoglycaemia in type 1 diabetes in a randomized crossover study of continuous intraperitoneal compared with subcutaneous insulin infusion." Diabetes, obesity and metabolism 11(11): 1001-1008 (2009).

Liu et al. "Insulin is a stronger inducer of insulin resistance than hyperglycemia in mice with type 1 diabetes mellitus (T1DM)." Journal of Biological Chemistry 284(40): 27090-27100 (2009).

Ljung. "System identification." Signal analysis and prediction. Birkhäuser, Boston, MA, 163-173 (1998).

Longman. "Iterative learning control and repetitive control for engineering practice." International journal of control 73 (10): 930-954 (2000).

Luo, "Machine learning of lifestyle data for diabetes." The University of Western Ontario. Electronic Thesis and Dissertation Repository, 3650 (2016).

Ly et al. "Day and night closed-loop control using the integrated Medtronic hybrid closed-loop system in type 1 diabetes at diabetes camp." Diabetes Care 38(7): 1205-1211 (2015).

Ly et al. "Automated overnight closed-loop control using a proportional-integral-derivative algorithm with insulin feedback in children and adolescents with type 1 diabetes at diabetes camp." Diabetes technology & therapeutics 18(6): 377-384 (2016).

Ly et al. "Automated hybrid closed-loop control with a proportional-integral-derivative based system in adolescents and adults with type 1 diabetes: individualizing settings for optimal performance." Pediatric diabetes 18(5): 348-355 (2017).

Maahs et al. "A randomized trial of a home system to reduce nocturnal hypoglycemia in type 1 diabetes." Diabetes care 37(7): 1885-1891 (2014).

Maahs et al. "Outcome measures for artificial pancreas clinical trials: a consensus report." Diabetes care 39(7): 1175-1179 (2016).

"Magni et al. ""Model predictive control of type 1 diabetes: an in silico trial."" Journal of Diabetes Science and Technology1:(6) 804-812 (2007)".

Magni et al. "Evaluating the efficacy of closed-loop glucose regulation via control-variability grid analysis." Journal of diabetes science and technology 2(4): 630-635 (2008).

Matsuo et al. "Strict glycemic control in diabetic dogs with closed-loop intraperitoneal insulin infusion algorithm designed for an artificial endocrine pancreas." Journal of Artificial Organs 6(1): 55-63 (2003).

McLaughlin et al. "Reversible hyperinsulinemic hypoglycemia after gastric bypass: a consequence of altered nutrient delivery." The Journal of Clinical Endocrinology & Metabolism 95(4): 1851-1855 (2010).

Mehta et al. "Impact of carbohydrate counting on glycemic control in children with type 1 diabetes." Diabetes Care 32(6): 1014-1016 (2009).

Messori et al., "A constrained model predictive controller for an artificial pancreas." IFAC Proceedings vols. 47(3):10144-10149 (2014).

Messori et al. "Individually adaptive artificial pancreas in subjects with type 1 diabetes: a one-month proof-of-concept trial in free-living conditions." Diabetes Technology & Therapeutics 19(10): 560-571 (2017).

Messori et al. "Individualized model predictive control for the artificial pancreas: In silico evaluation of closed-loop glucose control." IEEE Control Systems Magazine 38(1): 86-104 (2018).

Mingrone et al. "Bariatric-metabolic surgery versus conventional medical treatment in obese patients with type 2 diabetes: 5 year follow-up of an open-label, single-centre, randomised controlled trial." The Lancet 386(9997): 964-973 (2015).

Moore. "Iterative learning control: An overview." Iterative Learning Control for Deterministic Systems (371): 9-22 (1993).

Moreira et al. "Post-prandial hypoglycemia after bariatric surgery: pharmacological treatment with verapamil and acarbose." Obesity surgery 18(12):1618-1621 (2008).

Myers et al. "Intraportal glucose delivery enhances the effects of hepatic glucose load on net hepatic glucose uptake in vivo." The Journal of clinical investigation 88(1): 158-167 (1991).

Myint et al. "Prolonged successful therapy for hyperinsulinaemic hypoglycaemia after gastric bypass: the pathophysiological role of GLP1 and its response to a somatostatin analogue." European Journal of Endocrinology 166(5): 951-955 (2012).

Newswanger et al. "Development of a highly stable, nonaqueous glucagon formulation for delivery via infusion pump systems." Journal of diabetes science and technology 9(1): 24-33 (2015).

Nimri et al. "MD-Logic overnight control for 6 weeks of home use in patients with type 1 diabetes: randomized crossover trial." Diabetes care 37(11): 3025-3032 (2014).

(56) References Cited

OTHER PUBLICATIONS

Norrlöf. "Iterative Learning Control—Analysis, Design, and Experiments." Thesis No. 653, Linkoping Univ., Linkoping, Sweden (2000).

O'Kell et al. "Untargeted metabolomic analysis in naturally occurring canine diabetes mellitus identifies similarities to human Type 1 Diabetes." Scientific Reports 7(1): 1-7 (2017).

Owens et al. "Run-to-run control of blood glucose concentrations for people with type 1 diabetes mellitus." IEEE Transactions on Biomedical Engineering 53(6): 996-1005 (2006).

Palerm et al. "A run-to-run framework for prandial insulin dosing: handling real-life uncertainty." International Journal of Robust and Nonlinear Control: IFAC-Affiliated Journal 17(13): 1194-1213 (2007).

Palerm et al. "A run-to-run control strategy to adjust basal insulin infusion rates in type 1 diabetes." Journal of process control 18(3-4): 258-265 (2008).

Palerm. "Physiologic insulin delivery with insulin feedback: a control systems perspective." Computer methods and programs in biomedicine 102(2): 130-137 (2011).

Panteleon et al. "Quantification of delays associated with intraperitoneal insulin delivery and IV glucose sensing aiming at closed loop insulin delivery." Diabetes vol. 53(1701): Abstract 446-P (2004).

Panteleon et al. "Evaluation of the effect of gain on the meal response of an automated closed-loop insulin delivery system." Diabetes 55(7): 1995-2000 (2006).

Parker et al. "Advanced model predictive control (MPC) for type I diabetic patient blood glucose control." Proceedings of the 2000 American Control Conference. ACC. vol. 5. IEEE. 3483-3487(2000).

Patek et al., "Linear quadratic gaussian-based closed-loop control of type 1 diabetes", Journal of Diabetes Science and Technology 1(6): 834-841 (2007).

Patek et al. "Modular closed-loop control of diabetes." IEEE Transactions on Biomedical Engineering 59(11): 2986-2999 (2012).

Patti et al. "Hypoglycemia after gastric bypass: the dark side of GLP-1." Gastroenterology 146(3): 605-608 (2014).

Patti et al. "Insulin response to oral stimuli and glucose effectiveness increased in neuroglycopenia following gastric bypass." Obesity 23(4): 798-807 (2015).

Pernar et al. "Gastric bypass reversal: a 7-year experience." Surgery for Obesity and Related Diseases 12(8): 1492-1498 (2016).

Pickup. "Insulin pumps," Diabetes technology & therapeutics 18(S1): S22-S28 (2016).

Pinsker et al. "Randomized crossover comparison of personalized MPC and PID control algorithms for the artificial pancreas." Diabetes Care 39(7): 1135-1142 (2016).

Ranjan et al. "Effects of subcutaneous, low-dose glucagon on insulin-induced mild hypoglycaemia in patients with insulin pump treated type 1 diabetes." Diabetes, Obesity and Metabolism 18(4): 410-418 (2016).

* cited by examiner

```
┌─────────────────────────────────────────┐
│ Receiving glucose sensor data that      │
│ indicates a concentration of glucose    │
│ in a bloodstream of the patient 601     │
└─────────────────────────────────────────┘
                    ↓
┌─────────────────────────────────────────┐
│ Enacting an impeding glycemia protocol  │
│ based on the MPC in response to real    │
│ time glucose concentration 602          │
└─────────────────────────────────────────┘
                    ↓
┌─────────────────────────────────────────┐
│ Adapting a set of control parameters    │
│ using the relationships determined. 603 │
└─────────────────────────────────────────┘
                    ↓
┌─────────────────────────────────────────┐
│ Determining a dosage of glucose         │
│ altering substance to administer using  │
│ the zone MPC algorithm with the         │
│ control parameters in real time 604     │
└─────────────────────────────────────────┘
                    ↓
┌─────────────────────────────────────────┐
│ Sending a command to a pump 28 to       │
│ administer the dosage of the glucose    │
│ altering substance 605                  │
└─────────────────────────────────────────┘
```

FIG. 6

ADAPTIVE ZONE MODEL PREDICTIVE CONTROL WITH A GLUCOSE AND VELOCITY DEPENDENT DYNAMIC COST FUNCTION FOR AN ARTIFICIAL PANCREAS

CROSS REFERENCE TO RELATED APPLICATION

This application is a 35 U.S.C. § 371 National Phase Entry Application of International Application No. PCT/US2019/037923 filed Jun. 19 2019, which designates the U.S. and which claims the benefit under 35 U.S.C. § 119(e) to U.S. Provisional Application No. 62/686,931, filed on Jun. 19, 2018, the contents of each of which are hereby incorporated by reference in their entireties.

STATEMENT REGARDING FEDERALLY SPONSORED RESEARCH

This invention was made with government support under NIH Grant Nos. UC4DK108483 and DP3DK104057 awarded by the National Institutes of Health (NIH). The government has certain rights in the invention.

FIELD

The present invention is directed to glucose control systems. More specifically, the present invention is directed towards glucose monitoring (CGM) sensors and continuous subcutaneous insulin infusion systems.

BACKGROUND

Diabetes is a metabolic disorder that afflicts tens of millions of people throughout the world. Diabetes results from the inability of the body to properly utilize and metabolize carbohydrates, particularly glucose. Normally, the finely-tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock.

In patients with insulin-dependent diabetes, the symptoms of the disease can be controlled by administering additional insulin (or other agents that have similar effects) by injection or by external or implantable insulin pumps. The "correct" insulin dosage is a function of the level of glucose in the blood. Ideally, insulin administration should be continuously readjusted in response to changes in blood glucose level. In diabetes management, "insulin" instructs the body's cells to take in glucose from the blood. "Glucagon" acts opposite to insulin, and causes the liver to release glucose into the blood stream. The "basal rate" is the rate of continuous supply of insulin provided by an insulin delivery device (pump). The "bolus" is the specific amount of insulin that is given to raise blood concentration of the insulin to an effective level when needed (as opposed to continuous).

Presently, systems are available for continuously monitoring blood glucose levels by implanting a glucose sensitive probe into the patient. Such probes measure various properties of blood or other tissues, including optical absorption, electrochemical potential, and enzymatic products. The output of such sensors can be communicated to a hand held device that is used to calculate an appropriate dosage of insulin to be delivered into the blood stream in view of several factors, such as a patient's present glucose level, insulin usage rate, carbohydrates consumed or to be consumed, and exercise, among others. These calculations can then be used to control a pump that delivers the insulin, either at a controlled basal rate, or as a bolus. When provided as an integrated system, the continuous glucose monitor, controller, and pump work together to provide continuous glucose monitoring and insulin pump control.

Such systems at present require intervention by a patient to calculate and control the amount of insulin to be delivered. However, there may be periods when the patient is not able to adjust insulin delivery. For example, when the patient is sleeping, he or she cannot intervene in the delivery of insulin, yet control of a patient's glucose level is still necessary. A system capable of integrating and automating the functions of glucose monitoring and controlled insulin delivery would be useful in assisting patients in maintaining their glucose levels, especially during periods of the day when they are unable to intervene. A closed-loop system, also called the "artificial pancreas (AP), consists of three components: a glucose monitoring device such as a continuous glucose monitor ("CGM") that measures subcutaneous glucose concentration ("SC"); a titrating algorithm to compute the amount of analyte such as insulin and/or glucagon to be delivered; and one or more analyte pumps to deliver computed analyte doses subcutaneously.

In some known zone model predictive control (MPC) approaches to regulating glucose, the MPC penalizes the distance of predicted glucose states from a carefully designed safe zone based on clinical requirements. This helps avoid unnecessary control moves that reduce the risk of hypoglycemia. The zone MPC approach was originally developed based on an auto-regressive model with exogenous inputs, and was extended to consider a control-relevant state-space model and a diurnal periodic target zone. Specifically, an asymmetric cost function was utilized in the zone MPC to facilitate independent design for hyperglycemia and hypoglycemia.

Throughout the development and adaptation of the MPC approaches, different controller adaptation methods have been utilized for AP design. Earlier studies considered basal rate and meal bolus adaptation by using run-to-run approaches based on sparse blood glucose (BG) measurements. The availability of CGM further provided the opportunity of designing adaptive AP utilizing advanced feedback controllers. For instance, a nonlinear adaptive MPC has been proposed to maintain normoglycemia during fasting conditions using Bayesian model parameter estimation. In other examples, a generalized predictive control (GPC) approach that adopted a recursively updated subject model has been employed on a bi-hormone AP; this approach has also been explored to eliminate the need of meal or exercise announcements.

A model predictive iterative learning control approach has also been proposed to adapt controller behavior with patient's day-to-day lifestyle. In some approaches, a multiple model probabilistic predictive controller was developed to achieve improved meal detection and prediction. A dynamic insulin-on-board approach has also been proposed to compensate for the effect of diurnal insulin sensitivity variation. A switched linear parameter-varying approach was developed to adjust controller modes for hypoglycemia, hyperglycemia and euglycemia situations. A run-to-run approach was developed to adapt the basal insulin delivery rate and carbohydrate-to-insulin ratio by considering intra- and inter-day insulin sensitivity variability.

A major drawback in the proposed AP designs is the difficulty in achieving satisfactory blood glucose regulation in terms of hyperglycemia and hypoglycemia prevention through designing smart control algorithms.

SUMMARY

A system for the delivery of insulin to a patient is provided. The system includes a glucose sensor configured to provide a sensor glucose measurement signal representative of a real time glucose concentration. The system also includes an insulin delivery device configured to deliver insulin to a patient in response to control signals. The system also includes a controller programmed to receive the sensor glucose measurement signal from the glucose sensor. The sensor glucose measurement signal received indicates a concentration of the real time glucose concentration in a bloodstream. The controller is further configured to enact an impeding glycemia protocol based on a zone model predictive control (MPC) algorithm in response to the real time glucose concentration. The impeding glycemia protocol includes determining a relationship between predicted glucose concentrations, a rate of change of the predicted glucose concentrations, and a set of control parameters that determine insulin doses above and below a patient-specific basal rate. The relationship is designed offline without requiring online insulin or glucose data.

The controller is further configured to adapt the set of control parameters using the relationship determined. The controller is further configured to determine a dosage of glucose altering substance to administer, using the zone MPC algorithm with the control parameters, in real time. The controller is further configured to send a command to the insulin delivery device to administer the dosage of the glucose altering substance.

In some embodiments, the controller is further configured to decrease an insulin infusion increase rate in response to an increase of glucose state prediction when it is above a normal value, and decrease the insulin infusion increase rate in response to a decrease of glucose state prediction when the glucose state prediction is below the normal value. The controller is also configured to decrease the insulin infusion increase rate with the decrease of an absolute value of glucose velocity.

In some embodiments, the normal value is 110 mg/dL. The controller can also be configured to decrease insulin infusion to avoid hypoglycemia and decrease an insulin infusion increase rate in response to an increase of an absolute value of the glucose velocity. In other embodiments, the controller is further configured to process the data received at the glucose sensor to determine a set of real time glucose concentrations using a state observer to reduce the effect of noise on when measuring the real time glucose concentration. The set of real-time blood glucose measurements can be periodically determined by the glucose sensor.

In some embodiments, the set of parameters include control input penalties. The control input penalties can include separate sets of control input penalties for hyperglycemia and oglycemia.

In some embodiments, the glucose altering substance comprises at least one of insulin, pramlintide, or glucagon.

A method for providing closed loop adaptive glucose controller is also provided. The method includes receiving data from at least one glucose sensor, wherein the data received indicates a concentration of glucose in a bloodstream. The method also includes processing the data received to determine a real time glucose concentration and enacting an impeding glycemia protocol based on a zone model predictive control (MPC) algorithm in response to real time glucose concentration. The impeding glycemia protocol includes determining a relationship between predicted glucose concentrations, a rate of change of the predicted glucose concentrations, and a set of control parameters that determine insulin doses above and below a patient-specific basal rate. The method also includes adapting the set of control parameters using the relationships determined and determining a dosage of glucose altering substance to administer using the zone MPC algorithm with the control parameters in real time. The method also includes sending a command to a pump to administer the dosage of the glucose altering substance.

In some embodiments, the data is processed by a state observer to reduce noise on glucose concentration.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 6 illustrates a process for providing a closed loop adaptive glucose controller, in accordance with an embodiment of the present disclosure.

Figure 1A:
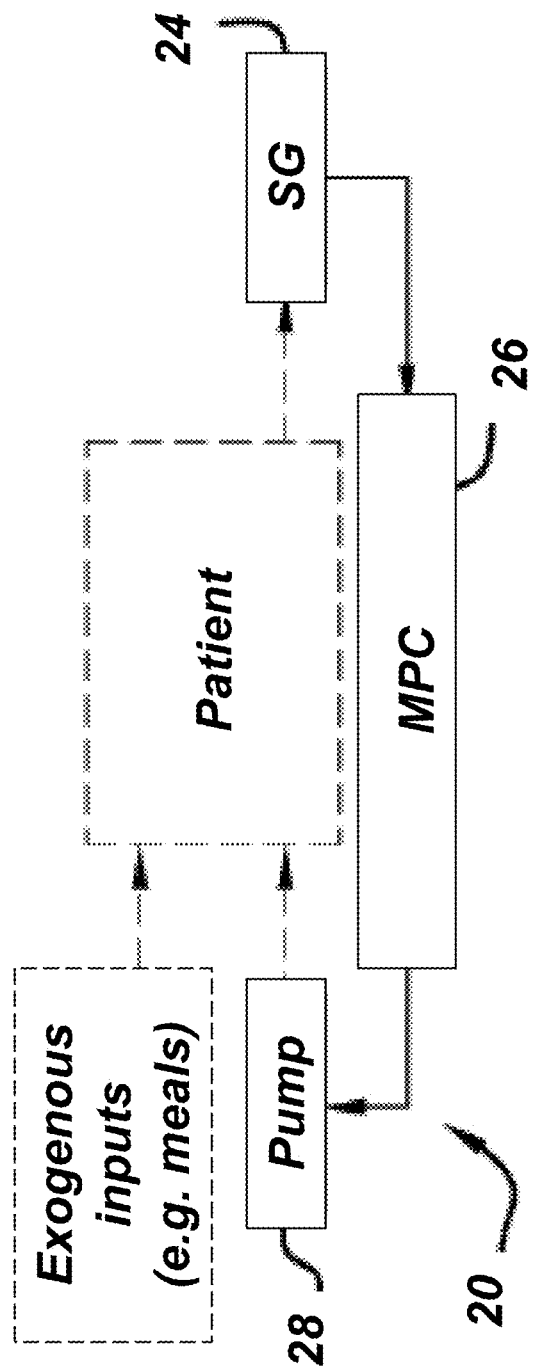
FIG. 1A illustrates a block diagram of a closed-loop insulin infusion system using a model predictive controller, in accordance with an embodiment of the disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

The present invention is described with reference to the attached figures, where like reference numerals are used throughout the figures to designate similar or equivalent elements. The figures are not drawn to scale, and they are provided merely to illustrate an instant embodiment. Several embodiments are described below with reference to example applications for illustration. It should be understood that numerous specific details, relationships, and methods are set forth to provide a full understanding of the disclosure. One having ordinary skill in the relevant art, however, will readily recognize that the disclosed embodiments can be practiced without one or more of the specific details, or with other methods. In other instances, well-known structures or operations are not shown in detail to avoid obscuring the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

FIG. 1A a basic block diagram of a closed-loop system 20 for continuous glucose monitoring and for continuous subcutaneous insulin infusion using a model predictive controller 26. The patient receives exogenous inputs, such as meals. The patient's glucose is measured 24, evaluated by the model predictive controller (MPC) and is used by the MPC to control a delivery device, such as a pump 28, to deliver medication to the patient to control blood glucose.

Figure 1B:
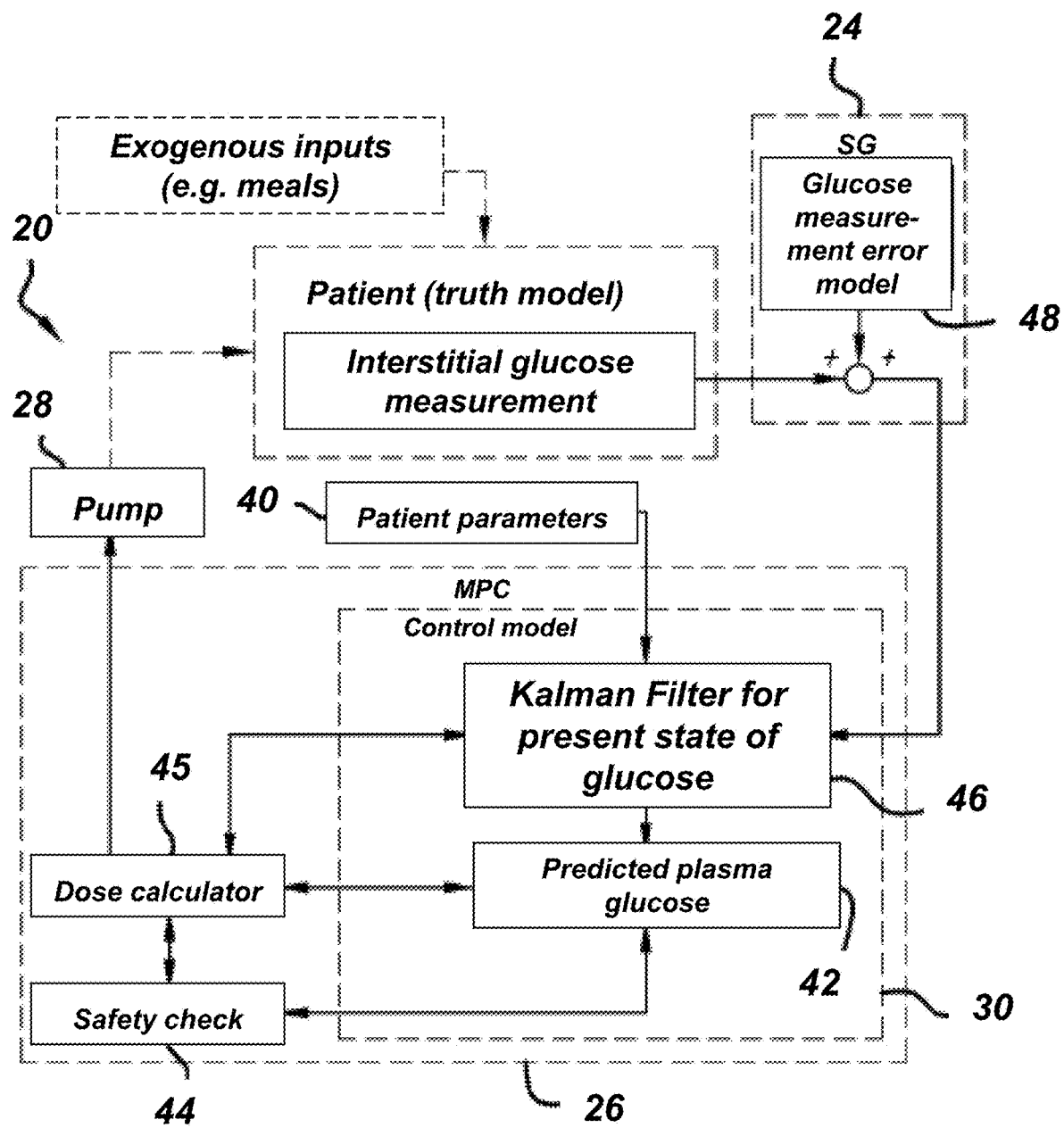
FIG. 1B illustrates a block diagram of a closed-loop insulin infusion system using a glucose measurement error model, in accordance with an embodiment of the disclosure.

Referring now to FIG. 1B, a control algorithm is used based on the model predictive control ("MPC") paradigm to deliver insulin in a closed-loop fashion. Interstitial glucose measurement occurs and every five minutes, simulated real-time sensor glucose ("SG") 24 was fed into the MPC controller 26, which calculated subcutaneous glucose concentration ("SC") insulin infusion for the insulin pump 28. A dose calculator 45 is included in this embodiment. The MPC controller 26 adopts a compartment model of incorporating dynamic control penalty adaptation in the zone MPC cost function and a constant prediction model. The SC insulin infusion can include insulin, pramlintide, or glucagon.

The MPC controller 26 adopts this compartment model by exploiting the dynamic relationship between insulin infusion and the predicted state and trend of blood glucose concentration. This approach is motivated by known multi-zone MPC designs. However, unlike the known multi-zone MPC designs, the present disclosure considers a continuous dependence of the control penalty parameters on both predicted values and trends of blood glucose. Specifically, an adaptive MPC cost function is proposed based on the values and change rates of glucose predictions. Moreover, explicit maps are constructed from the glucose prediction and its change rate to the input penalty parameters in the cost function. In addition, improved in silico results are obtained by the proposed adaptive method compared with the original zone MPC, in terms of mean glucose level and percentage time in the safe range, without increasing the risk of hypoglycemia.

A. Zone MPC

A periodic zone MPC algorithm with velocity-weighting and velocity-penalty for artificial pancreas has been developed to achieve safe and satisfactory closed-loop blood glucose regulation for patients with type 1 diabetes mellitus ("T1DM"). The algorithm is performed every 5 minutes driven by glucose measurements. At a controller update time instant i, the control law of the zone MPC with velocity-weighting and velocity-penalty is obtained by solving the following con-strained optimization problem:

$$u^*_{0:N_u-1} := \arg\min_{u_{0:N_u-1}} J(x_i, u_{0:N_u-1}) \quad (1)$$

with cost function $$J(\cdot,\cdot) \Sigma_{k=1}^{N_p}(\hat{z}_k^2 + Q(v_k)\hat{z}_k^2 + \check{D}\hat{v}_k^2) + \Sigma_{k=1}^{N_u-1}(\hat{R}\hat{u}_k^2 + \check{R}\check{u}_k^2) \quad (2)$$

subject to constraints $$x_0 = x_i \quad (3a)$$

$$x_{k+1} = Ax_k + Bu_k \quad \forall k \in Z_{0:N_p-1} \quad (3b)$$

$$y_k = C_y x_k \quad \forall k \in Z_{0:N_p} \quad (3c)$$

$$v_k = C_v x_k \quad \forall k \in Z_{0:N_p} \quad (3d)$$

$$u_k \leq \hat{\zeta}_{i+k} \quad \forall k \in Z_{0:N_u-1} \quad (3e)$$

$$u_k \geq \check{\zeta}_{i+k} \quad \forall k \in Z_{0:N_u-1} \quad (3f)$$

$$u_k = 0 \quad \forall k \in Z_{N_u:N_p-1} \quad (3g)$$

$$z_k := Z(y_k, i+k) \quad \forall k \in Z_{0:N_p} \quad (3h)$$

$$\hat{z}_k := \max(z_k, 0) \quad \forall k \in Z_{0:N_p} \quad (3i)$$

$$\check{z}_k := \min(z_k, 0) \quad \forall k \in Z_{0:N_p} \quad (3j)$$

$$\hat{u}_k := \max(u_k, 0) \quad \forall k \in Z_{0:N_u-1} \quad (3k)$$

$$\check{u}_k := \min(z_k, 0) \quad \forall k \in Z_{0:N_u-1} \quad (3l)$$

$$\hat{v}_k := \max(v_k, 0) \quad \forall k \in Z_{0:N_p} \quad (3m)$$

$$\check{D} = \begin{cases} D > 0 & \text{if } \hat{y}_0 + y_s \in \mathbb{D} \\ 0 & \text{otherwise} \end{cases} \quad (3n)$$

In eq. (2), $Q(v_k)$ denotes a velocity-dependent weighting matrix [8] satisfying $$Q(v) = \begin{cases} 1 & \text{if } v \geq 0 \\ \epsilon & \text{if } v \leq 1 \\ \frac{1}{2}[\cos v\pi(1-\epsilon) + (1+\epsilon)] & \text{otherwise} \end{cases} \quad (4)$$

Parameter $\check{D}$ in (2) determines a glucose dependent cost on glucose velocity, and is defined in (3n) with $\mathbb{D} := [140, 180]$ and $D := 1000$. The prediction horizon and control horizon satisfies $N_p := 9$ and $N_u := 5$, which correspond to 45 and 25 minutes, respectively, and the control input weighting parameters are set to $\hat{R} := 6500$ and $\check{R} := 100$, respectively. The state space model in (3b)-(3d) satisfies $$A := \begin{bmatrix} p_1 + 2p_2 & -2p_1p_2 - p_2^2 & p_1p_2^2 \\ 1 & 0 & 0 \\ 0 & 1 & 0 \end{bmatrix},$$

$$B := \frac{1800\,K}{u_{TDI}}[1\ 0\ 0]_\cdot,$$

$$C_y := [0\ 0\ 1],$$

$$C_v := [0.1\ 0\ -0.1],$$

$$K := 90(p_1 - 1)(p_2 - 1)^2, \ p_1 := 0.98, \ p_2 := 0.965.$$

Here $u_{TDI}$ denotes the subject-specific total daily insulin; $\hat{\zeta}_{i+k}$ and $\check{\zeta}_{i+k}$ in (3e)-(3f) denote the upper and lower bounds on the control input $u_k$. In eq. (3h), the function $Z(y, i)$ is defined as $$Z(y,i) := \arg\min_{\alpha \in \mathbb{R}} \{\alpha^2 | y - \alpha \in [\check{\zeta}_i, \hat{\zeta}_i]\},$$

where $[\check{\zeta}_i, \hat{\zeta}_i]$ represents the diurnal glucose target zone. In particular, we note that $u_k$ in the MPC optimization problem denotes the relative correction of insulin infusion $u_{abs,k}$ from the basal rate $u_{basal}$, namely, $u_k := u_{abs,k} - u_{basal}$. As the amount of insulin infusion is non-negative, it holds that $\zeta_{i+k} \geq u_{basal}$ and $u_k \geq -u_{basal}$. By definition, $\hat{u}_k$ and $\check{u}_k$ indicate delivery rates above and below basal rate, respectively, and thus control input weighting parameters $\hat{R}$ and $\check{R}$ separately penalize the costs of delivering insulin bolus above and below insulin. As short periods of time in hypoglycemia can lead to severe health risks such as seizures, coma and even death, the values of $\hat{R}$ and $\check{R}$ are chosen to satisfy $\hat{R} << \check{R}$ to ensure safety and encourage prompt pump suspension when providing less insulin does not cause severe hyperglycemia but does reduce the risk of hypoglycemia.

B. Adaptive Zone MPC Design

A few key parameters of the MPC algorithm (e.g., the prediction horizon $N_p$, the control horizon $N_u$ and the control input penalties $\hat{R}$ and $\check{R}$) were set to constant. The present application demonstrates that improved performance can be obtained by further adapting some of these parameters. Since the choice of the prediction and control horizons depend on 1) the amount of model mismatch between the state space model in (3b)-(3d) and the subject to which the controller is applied and 2) the amount of computation resources allocated for solving the MPC optimization problem on an artificial pancreas, the design of $\hat{R}$ and $\check{R}$ parameters are the primal focus of the present disclosure. The design of $\hat{R}$ and $\check{R}$ parameters has a clear and more direct relation with the control performance—smaller values of $\hat{R}$ and $\check{R}$ correspond to more aggressive controller activity and vice versa. As a result, the present disclosure provides an efficient method of adapting the $\hat{R}$ and $\check{R}$ parameters, to achieve improved control performance in terms of percent time in safe range [70, 180] mg/dL and average blood glucose level without increasing the risk of hypoglycemia.

The risk of insulin infusion on hypoglycemia varies with the state and trend of the subject's blood glucose concentration. When the glucose concentration rises above the safe range, the higher the blood glucose concentration, the more likely that a relatively large amount of insulin has been infused but has not appeared in plasma due to the delayed effect of subcutaneous insulin injection. Thus, it is more probable that the blood glucose is able to decrease to the safe range without further insulin infusion.

In this case, if the controller maintains the same degree of responsiveness, the delayed insulin effect would culminate in controller-induced hypoglycemia. The present disclosure addresses dynamically adjusting MPC weighing parameters, in tandem with IOB constraints to ensure enhanced safety. On the other hand, given the same glucose concentration but with a correctly-predicted rapidly increasing (rather than decreasing or almost stationary) trend, it is comparably safer to further infuse a cautiously-designed amount of insulin based on the predicted glucose trend, which indicates additional insulin is needed to regulate the excessive glucose. Based on these considerations, the values of $\hat{R}$ and $\check{R}$ should be adjusted in accordance with both the glucose state prediction $y_k$ [obtained via (3b)-(3b)] and glucose velocity $$\mu_k := y_k - y_{k-1} \quad (5)$$

to achieve improved glucose regulation. $\hat{R}$- and $\check{R}$-surfaces are designed along continuum values of glucose prediction $y_k$ and velocity $\mu_k$. As a result, the MPC cost function switches from its original form in (2) to $$J(\cdot,\cdot) = \Sigma_{k=1}^{N_p}(\check{z}_k^2 + Q(v_k)\hat{z}_k^2 + \hat{D}\hat{v}_k^2) + \Sigma_{k=1}^{N_u-1}(\hat{R}(\mu_k, y_k)\hat{u}_k^2 + \check{R}(\mu_k, y_k)\check{u}_k^2) \quad (6)$$

C. Design of $\hat{R}(\mu_k, y_k)$

From the definition of $\hat{u}_k$ in (3k), $\hat{R}(\mu_k, y_k)$ in (6) controls insulin infusion above the basal rate and is usually in effect when $y_k > 80$. Due to the asymmetry of the blood glucose profile, however, it determines both glucose regulation performance and hypoglycemia risk and therefore is the major focus of parameter adaptation. To separately consider the scenarios of ascending and descending glucose sequences, $\hat{R}(\mu_k, y_k)$ is parameterized according to the sign of predicted glucose velocity $\mu_k$:

$$\hat{R}(\mu_k, y_k) := \begin{cases} \hat{R}^+(\mu_k, y_k, \theta^+) & \text{if } \mu_k \geq 0, \\ \hat{R}^-(\mu_k, y_k, \theta^-) & \text{if } \mu_k < 0, \end{cases} \quad (7)$$

where $\theta^+$ and $\theta^-$ are two vector-valued parameters that determine the relationship of $\hat{R}^+$ and $\hat{R}^-$ with $\mu_k$ and $y_k$, respectively. In this work, $\hat{R}^+(\mu_k, y_k, \theta^+)$ and $\hat{R}^-(\mu_k, y_k, \theta^-)$ are designed by using an identical approach, but are parameterized with different parameters $\theta^+$ and $\theta^-$ due to their different roles in glucose regulation. Concretely, the principles of designing $\hat{R}^+(\mu_k, y_k, \theta^+)$ are to ensure that A1) given the same (positive) glucose velocity prediction, the responsiveness of the controller (in terms of increasing insulin infusion rate) should decrease with the increase of glucose state prediction when it is above its normal value (say, 110 mg/dL), and decrease with the decrease of glucose state prediction when it is below its normal value; and A2) given the same glucose state prediction, the responsiveness of the controller should decrease with the decrease of the absolute value of glucose velocity.

On the other hand, the principles for $\hat{R}^-(\mu_k, y_k, \theta^-)$ design include B1) given a negative glucose velocity prediction, the controller should decrease insulin infusion to avoid hypoglycemia, and should be even more cautious when the corresponding glucose predictions are low or extremely high;

B2) given the same glucose prediction, the responsiveness of the controller should decrease with the increase of the absolute value of the glucose velocity.

These principles reflect the clinical safety requirements in blood glucose regulation, while still providing an opportunity to enhance control performance by exploiting glucose state and velocity dependent controller adaptation. To implement these principles, the present disclosure provides a two-step design approach:

S1) build bowl-shaped $y_k$-dependent upper and lower bounds for $\hat{R}^+(\mu_k, y_k, \theta^+)$ and $\hat{R}^-(\mu_k, y_k, \theta^-)$ by considering the two limiting cases $\mu_k = 0$ and $\mu_k \to \infty$, respectively, so that items A1 and B1 in the design principles can be ensured;

S2) vary the values of these functions monotonically between the upper and lower bounds for different values of $\mu_k$, to accommodate principles A2 and B2.

Specifically, the upper and lower bounds $\overline{\mathfrak{R}}^+(y_k, \theta^+)$ and $\underline{\mathfrak{R}}^+(y_k, \theta^+)$ for $\hat{R}^+(\mu_k, y_k, \theta^-)$ are proposed as $$\overline{\mathfrak{R}}^+(y_k, \theta^+) := \begin{cases} \min\{\delta_H^+, \exp[[a_{1H}^+(y_k - \eta^+)]^{a_H^+}] + b_{1H}^+\} & \text{if } y_k \geq \eta^+, \\ \min\{\delta_H^+, \exp[a_{2H}^+(\eta^+ - y_k)] + b_{2H}^+\} & \text{if } y_k < \eta^+, \end{cases} \quad (8)$$

-continued $$\underline{R}^+(y_k, \theta^+) := \begin{cases} \min\{\delta_L^+, \exp[[a_{1L}^+(y_k - \eta^+)]^{\alpha_L^+}] + b_{1L}^+\} & \text{if } y_k \geq \eta^+, \\ \min\{\delta_L^+, \exp[a_{2L}^+(\eta^+ - y_k)] + b_{2L}^+\} & \text{if } y_k < \eta^+, \end{cases} \quad (9)$$

respectively, with $b_{2H}^+ := b_{1H}^+ - 1$, $b_{2L}^+ := b_{1L}^+ - 1$ and $\delta_H^+$, $a_{1H}^+$, $a_{2H}^+$, $b_{1H}^+$, $\alpha_H^+$, $\delta_L^+$, $a_{1L}^+$, $a_{2L}^+$, $b_{1L}^+$, $\alpha_L^+$ and $\eta^+$ being elements in $\theta^+$. Similarly, the upper and lower bounds $\overline{\mathfrak{R}}^-(y_k, \theta^-)$ and $\underline{\mathfrak{R}}^-(y_k, \theta^-)$ for $\hat{R}^-(\mu_k, y_k, \theta^-)$ are defined as $$\overline{R}^-(y_k, \theta^-) := \begin{cases} \min\{\delta_H^-, \exp[[a_{1H}^-(y_k - \eta^-)]^{\alpha_H^-}] + b_{1H}^-\} & \text{if } y_k \geq \eta^-, \\ \min\{\delta_H^-, \exp[a_{2H}^-(\eta^- + 400 - y_k)] + b_{2H}^-\} & \text{if } y_k < \eta^-, \end{cases} \quad (10)$$

$$\underline{R}^-(y_k, \theta^-) := \begin{cases} \min\{\delta_L^-, \exp[[a_{1L}^-(y_k - \eta^-)]^{\alpha_L^-}] + b_{1L}^-\} & \text{if } y_k \geq \eta^-, \\ \min\{\delta_L^-, \exp[a_{2L}^-(\eta^- + 400 - y_k)] + b_{2L}^-\} & \text{if } y_k < \eta^-, \end{cases} \quad (11)$$

with $b_{2H}^- := b_{1H}^- - \exp(400 \times a_{2H}^-)$, $b_{2L}^- := b_{1L}^- - \exp(400 \times a_{2L}^-)$ and $\delta_H^-$, $a_{1H}^-$, $a_{2H}^-$, $b_{1H}^-$, $\alpha_H^-$, $\delta_L^-$, $a_{1L}^-$, $a_{2L}^-$, $b_{1L}^-$, $\alpha_L^-$ and $\eta^-$ being elements of $\theta^-$. This completes Step S1.

Based on the bounds in (8)-(11), the velocity and state dependent weighting parameters $\hat{R}^+(\mu_k, y_k, \theta^+)$ and $\hat{R}^-(\mu_k, y_k, \theta^-)$ are evaluated according to $$\hat{R}^+(\mu_k, y_k, \theta^+) := \overline{\mathfrak{R}}^+(y_k, \theta^+) + \exp(-\tau^+ \mu_k)[\underline{\mathfrak{R}}^+(y_k, \theta^+) - \overline{\mathfrak{R}}^+(y_k, \theta^+)], \quad (12)$$

$$\hat{R}^-(\mu_k, y_k, \theta^-) := \overline{\mathfrak{R}}^-(y_k, \theta^-) - \exp(-\tau^- \mu_k)[\underline{\mathfrak{R}}^-(y_k, \theta^-) - \overline{\mathfrak{R}}^-(y_k, \theta^-)], \quad (13)$$

where $\tau^+$ and $\tau^-$ are elements in $\theta^+$ and $\theta^-$, respectively. This completes Step S2.

Now interpretations for $\hat{R}^+(\mu_k, y_k, \theta^+)$ and $\hat{R}^-(\mu_k, y_k, \theta^-)$ are provided through explaining their parameters $\theta^+$ and $\theta^-$, which are given by $$\theta^+ := [\delta_H^+, a_{1H}^+, a_{2H}^+, b_{1H}^+, \alpha_H^+, \delta_L^+, a_{1L}^+, a_{2L}^+, b_{1L}^+, \alpha_L^+, \tau^+, \eta^+]$$

$$\theta^- := [\delta_H^-, a_{1H}^-, a_{2H}^-, b_{1H}^-, \alpha_H^-, \delta_L^-, a_{1L}^-, a_{2L}^-, b_{1L}^-, \alpha_L^-, \tau^-, \eta^-].$$

To understand the roles of different parameters, we first note that the "+" and "−" symbols in the superscripts separately indicate the cases "$\mu_k \geq 0$" and "$\mu_k < 0$", and that "H" and "L" in the subscripts represent upper bounds and lower bounds, respectively. Second, $\tau^+$ and $\tau^-$ control the decay rates of $\hat{R}^+(\mu_k, y_k, \theta^+)$ and $\hat{R}^-(\mu_k, y_k, \theta^-)$ with respect to glucose velocity $\mu_k$. See (12)-(13). For the rest of the parameters, $\theta^+$ and $\theta^-$ are each composed of different parameterizations of a simpler pattern $[\delta, a_1, a_2, b_1, \alpha, \eta]$, which defines a bowl-shaped curve $Y(y)$ composed of two exponential functions with saturation:

$$Y(y) := \begin{cases} \min\{\delta, \exp[a_2(\eta - y + \ell)] + [b_1 - \exp(a_2 \ell)]\}, & \text{if } y \leq \eta, \\ \min\{\delta, \exp[a_1(y - \eta)^{\alpha}] + b_1\}, & \text{otherwise,} \end{cases} \quad (14)$$

In particular, $\delta$ determines the maximum (saturation) value of the curve, $b_1$ denotes the minimum value of the curve, $a_1$ and $\alpha$ determine the "steepness" of the "right-hand side" (namely, $y > \eta$) exponential function, $a_2$ determines the "steepness" of the "left-hand side" exponential function, and $\eta$ decides the conjunction point of the two exponential functions. Note that $l=0$ for (8)-(9) and $l=400$ for (10)-(11).

Figure 2:
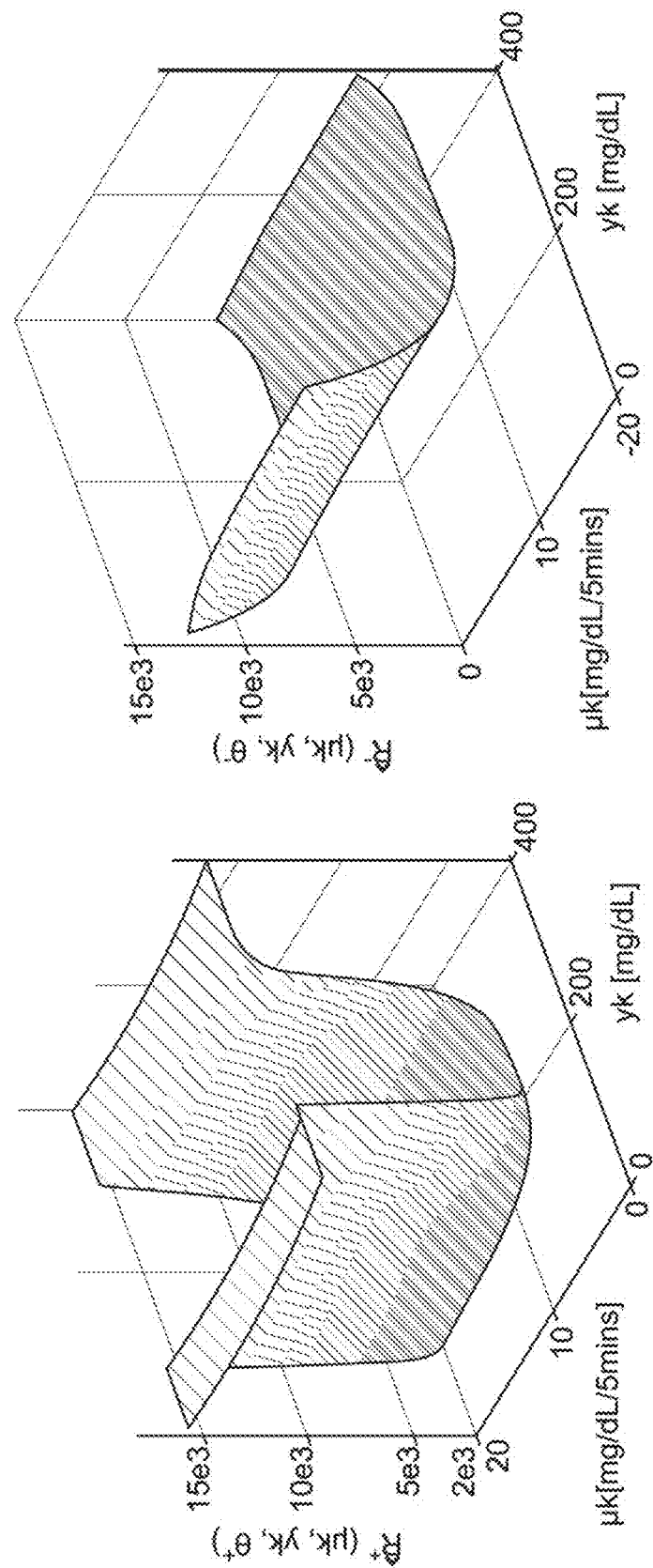
FIG. 2 is a graphical illustration of the parameters $\theta^+$ and $\theta^-$ that impact the infusion rate of insulin, in accordance with an embodiment of the present embodiment.

Based on the above interpretations, the parameters in $\theta^+$ and $\theta^-$ are designed for improved glucose regulation performance. FIG. 2 is a graphical illustration of the parameters $\theta^+$ and $\theta^-$ that impact the infusion rate of insulin, in accordance with an embodiment of the present embodiment. The parameters $\theta^+$ and $\theta^-$ are iteratively optimized using the 10-patient cohort of the UVA/Padova simulator with the goal of achieving improved mean glucose values without increasing the risk of hypoglycemia, following a 24-hour in silico protocol with 3 unannounced meals of [50, 75, 75] g carbohydrate (CHO) at 08:00, 12:00 and 19:00, respectively. The obtained design also goes through stress tests for scenarios of different measurement noises, basal rate mismatches, secret insulin boluses (used to simulate the effect of exercise), and over/underestimated meal boluses. The values of the obtained parameters are provided in TABLE I. FIG. 2 illustrates the relationship of $\hat{R}^+(\mu_k, y_k, \theta^+)$ and $\hat{R}^-(\mu_k, y_k, \theta^-)$ with glucose state $y_k$ and glucose velocity $\mu_k$.

D. Design of $\check{R}(\mu_k, y_k)$

From (31), $\hat{R}(\mu_k, y_k)$ affects insulin infusion below the basal rate, which critically determines controller actions when the glucose concentration drifts toward or falls into the hypoglycemia region ($y_k < 70$ mg/dL). The proposed approach to designing $\hat{R}(\mu_k, y_k)$ equally applies to $\check{R}(\mu_k, y_k)$. As detailed above, $\check{R}$ in (2) is usually set to a small value ($\check{R}=100$) to encourage proper pump suspensions to avoid hypoglycemia. To enhance this safety concern, it suffices to consider the following simple glucose-dependent multi-zone parameter adaptation formula:

$$\check{R}(y_k) := \begin{cases} 100, & \text{if } y_k > 140, \\ 10, & \text{if } y_k \in [120, 140], \\ 1, & \text{if } y_k < 120. \end{cases} \quad (15)$$

Here a short-hand notation $\check{R}(y_k)$ is used instead of $\check{R}(\mu_k, y_k)$ as the effect of glucose velocity is not considered in this case. The implication is that an active pump suspension strategy is enforced when the glucose prediction is conspicuously low, regardless of the glucose velocity $\mu_k$.

E. Implementation

In terms of implementation, the proposed adaptive MPC method basically replaces the original cost function in (2) with (6), which adds to the non-convexity of the MPC optimization problem. To ensure the convergence of the optimization algorithm and speed up the computation, a heuristic technique is introduced to implement the proposed adaptive MPC based on the physiological properties of the insulin-glucose metabolic process. To aid the description, the notation $\{\bullet\}_i$ is used to denote a data sequence obtained by the zone MPC at controller update time instant i (e.g., $\{y_k : k \in \mathbb{Z}_{0:N_u-1}\}_i$). The motivating observation is that a lag of 10-30 minutes exists between the plasma insulin concentrations and the effect of insulin. As the control horizon $N_u$ is equal to 5 and the sampling time is 5 minutes, the predictions $\{y_k : k \in \mathbb{Z}_{0:N_u-1}\}_i$ and $\{\mu_k : k \in \mathbb{Z}_{0:N_u-1}\}_i$ are dominated by the historical glucose measurements at time instant i rather than the optimal inputs $\{u_k^*\}_i$. In this regard, $\{y_k : k \in \mathbb{Z}_{0:N_u-1}\}_i$ and $\{\mu_k : k \in \mathbb{Z}_{0:N_u-1}\}_i$ is estimated with $\{y_k : k \in \mathbb{Z}_{1:N_u}\}_{i-1}$ and $\{y_k - y_{k-1} : k \in \mathbb{Z}_{1:N_u}\}_i$, respectively, and $\{\hat{R}(\mu_k, y_k) : k \in \mathbb{Z}_{0:N_u-1}\}_i$ is calculated based on the obtained estimates for $\{y_k : k \in \mathbb{Z}_{0:N_u-1}\}_i$ and $\{\mu_k : k \in \mathbb{Z}_{0:N_u-1}\}_i$. An important property of these estimates is that they can be calculated before solving the MPC optimization problem [formed by (1), (6) and (3)] at time instant i and are constant during the solution procedure of the optimization problem.

As illustrated herein, the glucose velocity sequence $\{\mu_k\}$ adopted herein differs from $\{v_k\}$ defined according to (3d), which is typically used to quantify the velocity weighting and velocity penalties. By definition, $\{\mu_k\}$ provides a closer approximation of the velocity sequence of the noiseless glucose prediction $\{y_k\}$. Another major consideration here, however, is to avoid introducing $\{\mu_k\}$-induced disturbances to the convergence of the $\{v_k\}$-driven sequential optimization procedure utilized to solve non-convex MPC optimization problem. In particular, during the sequential optimization procedure, the sequence $\{v_k\}$ is updated in each iteration until the convergence conditions are satisfied. As the estimates for $\{\mu_k\}$ remain constant and do not change with $\{v_k\}$ throughout this disclosure, the adopted $\{\mu_k\}$ sequence does not affect the convergence of the sequential optimization algorithm.

Figure 3:
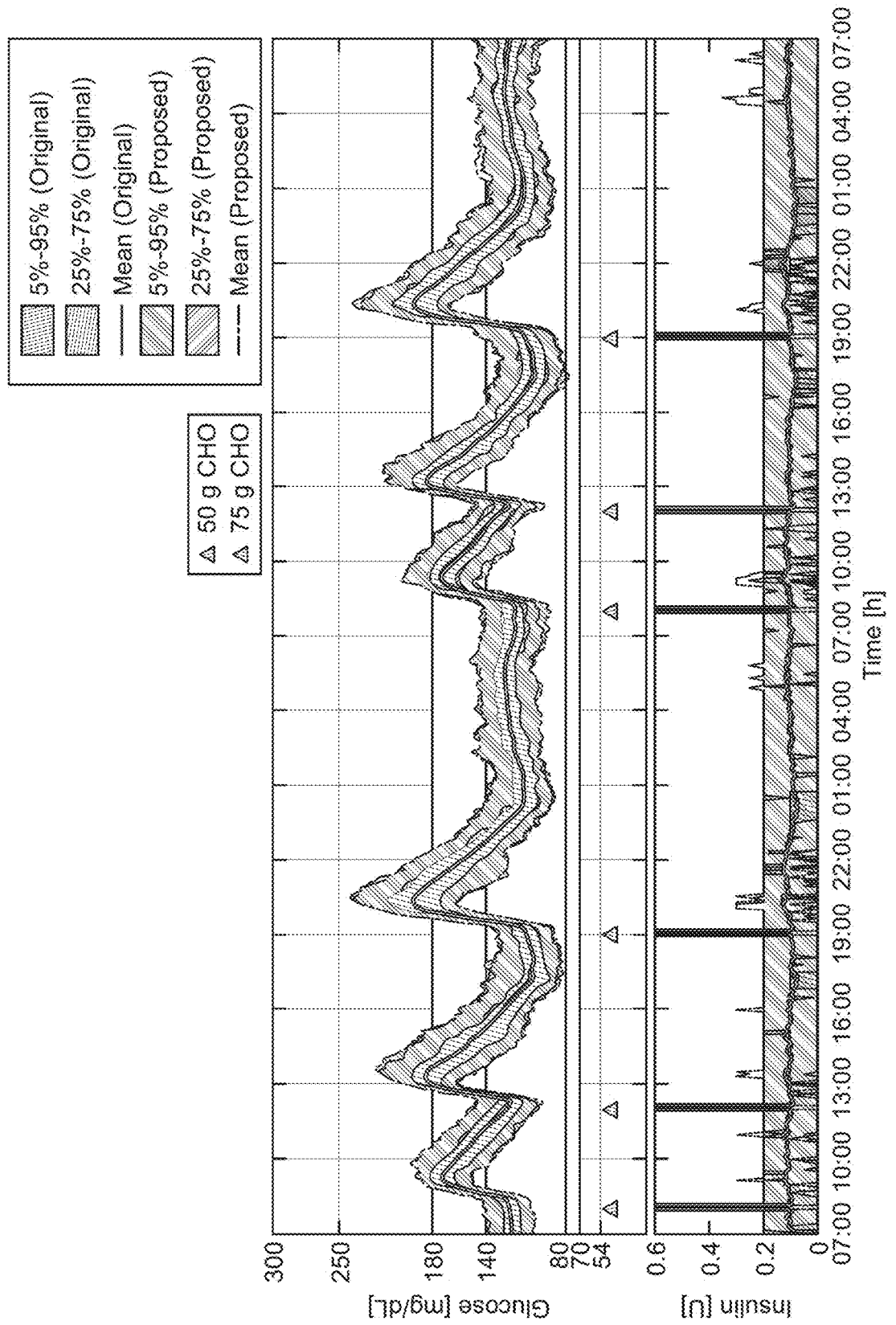
FIG. 3 is a graphical illustration of a proposed adaptive method with the original zone-MPC developed for announced meals, in accordance with the present embodiment.
Figure 4:
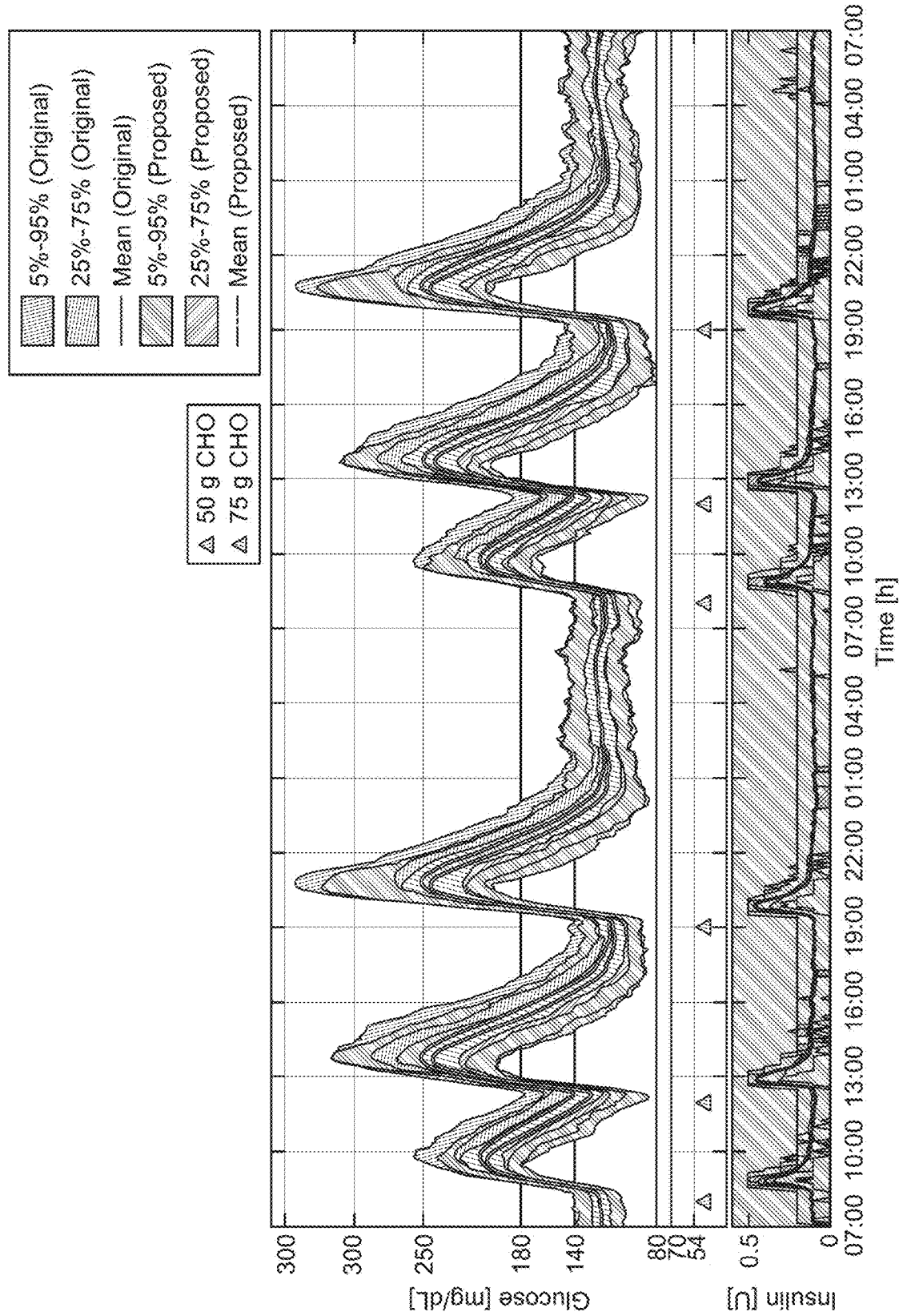
FIG. 4 is a graphical comparison between the proposed adaptive method with the original zone-MPC developed for unannounced meals, in accordance with an embodiment of the present embodiment.

The safety and effectiveness of the proposed method is evaluated on the 10-patient cohort of the FDA-accepted UVA/Padova metabolic simulator through comparisons with the original zone MPC. FIG. 3 is a graphical illustration of a proposed adaptive method with the original zone-MPC developed for announced meals, in accordance with the present embodiment. FIG. 4 is a graphical comparison between the proposed adaptive method with the original zone-MPC developed for unannounced meals, in accordance with an embodiment of the present embodiment. As an initial parameter, a 48-hour 6-meal protocol starting from 7:00 on Day 1 is considered. On each day, breakfast (50 g CHO), lunch (75 g CHO) and dinner (75 g CHO) are consumed at 8:00, 13:00 and 17:00, respectively. Two controllers are compared, including the original zone MPC and the proposed adaptive zone MPC with parameter setting in TABLE I. The performance of each controller is evaluated according to the introduced protocol for 10 times by considering random additive CGM measurement noises using random seeds 1 through 10 (for the whole 10-patient cohort). The performance of each controller is evaluated by separately considering the scenarios with and without meal announcements. A total of 200 simulations are performed for each controller. The 5%, 25%, 50%, 75% and 95% quartile curves are presented in FIGS. 3 and 4. Furthermore, a comparison of the statistics is provided in Tables II-III.

The performance comparison of the original zone MPC with the proposed adaptive zone MPC is provided in FIG. 3 and TABLE II below for the scenario of announced meals. Both controllers achieve satisfactory performance for hypoglycemia prevention measured by percent time <70 mg/dL and percent time <54 mg/dL (severe hypoglycemia). In particular, a comparison of the values of these two performance metrics indicates that the proposed approach does not introduce increased risk for hypoglycemia. In general, with meal announcements, the glucose response is dominated by meal boluses and the effect of closed-loop control on glucose regulation is restricted, particularly given that the original zone MPC already achieved good control performance for announced meals. As a result, the proposed adaptive approach only leads to a small performance improvement in terms of percent time in the euglycemic range of 70-180 mg/dL (91.2% vs. 90.9%; p<0.001), and mean glucose (135.6 mg/dL vs. 136.5 mg/dL; p<0.001). The proposed controller appears to have slightly increased risk of hyperglycemia (percent time >250 mg/dL, 0.1% vs. 0.0%; p=0.526), but the p value indicates that this observation may not have statistical significance.

TABLE I

| | Parameters for $\theta^+$ and $\theta^-$ | | | | | | | | | | | |
|---|---|---|---|---|---|---|---|---|---|---|---|---|
| | $\delta^+_H$ | $\alpha_{1H}^+$ | $\alpha_{2H}^+$ | $b_{1H}^+$ | $\alpha_H^+$ | $\delta_L^+$ | $\alpha_{1L}^+$ | $\alpha_{2L}^+$ | $b_{1L}^+$ | $\alpha_L^+$ | $\tau^+$ | $\eta^+$ |
| Value | 16,500 | 0.14 | 0.32 | 5500 | 0.75 | 15,500 | 0.11 | 0.20 | 2,000 | 0.75 | 0.20 | 130 |
| | $\delta_H^-$ | $\alpha_{1H}^-$ | $\alpha_{2H}^-$ | $b_{1H}^-$ | $\alpha_H^-$ | $\delta_L^-$ | $\alpha_{1L}^-$ | $\alpha_{2L}^-$ | $b_{1L}^-$ | $\alpha_L^-$ | $\tau^-$ | $\eta^-$ |
| Value | 1,000,000 | 0.03 | 0.02 | 5,000 | 1 | 1,000,000 | 0.03 | 0.02 | 4910 | 1 | 0.20 | 180 |

TABLE II

Glycemic metrics comparing the proposed method with the original zone MPC (announced meals)

| #Simulations = 100 % time | Day and night Metric | | | Overnight (24:00-06:00 h) | | |
|---|---|---|---|---|---|---|
| | Original | Proposed | p value | Original | Proposed | p value |
| <54 mg/dL | 0 (0) | 0 (0) | — | 0 (0) | 0 (0) | — |
| <70 mg/dL | 0 (0.2) | 0 (0.2) | 0.346 | 0 (0) | 0 (0.2) | 0.32 |
| 70-180 mg/dL | 90.9 (6) | 91.2 (5.8) | 0.04 | 100 (0.1) | 100 (0.2) | 0.811 |
| >250 mg/dL | 0 (0.3) | 0.1 (0.3) | 0.526 | 0 (0) | 0 (0) | — |
| Mean glucose (mg/dL) | 136.5 (5.6) | 135.6 (5.4) | <0.001 | 119.4 (5.2) | 119.1 (5.1) | 0.011 |
| SD glucose (mg/dL) | 28 (5.2) | 45.1 (10.2) | <0.001 | 12.9 (3.1) | 13.4 (3.4) | <0.001 |
| Path length | 3597.6 (101.4) | 3607.1 (105.9) | <0.001 | 841 (19.7) | 842.9 (20.3) | <0.001 |
| Mean glucose at 07:00 h (mg/dL) | 121.1 (8.5) | 119.8 (8.9) | <0.001 | — | — | — |

Data in this table are shown as mean (standard deviation). Statistical significance is assessed by paired t-test.

TABLE III

Glycemic metrics comparing the proposed method with the original zone MPC (unannounced meals)

| #Simulations = 100 % time | Day and night | | | Overnight (24:00-06:00 h) | | |
|---|---|---|---|---|---|---|
| | Original | Proposed | p value | Original | Proposed | p value |
| <54 mg/dL | 0 (0) | 0 (0) | — | 0 (0) | 0 (0) | — |
| <70 mg/dL | 0 (0.2) | 0 (0.1) | 0.788 | 0 (0.1) | 0 (0.1) | 0.752 |
| 70-180 mg/dL | 67.5 (9.9) | 72.7 (8.6) | <0.001 | 99.7 (0.9) | 100 (0.1) | 0.015 |
| >250 mg/dL | 6.4 (7.6) | 4.5 (5.6) | <0.001 | 0 (0) | 0 (0) | — |
| Mean glucose (mg/dL) | 160.7 (14.5) | 154.2 (12.1) | <0.001 | 122.3 (6.7) | 120.9 (5.4) | <0.001 |
| SD glucose (mg/dL) | 47.9 (10.8) | 45.1 (10.2) | <0.001 | 14.2 (3.3) | 13.2 (3.1) | <0.001 |
| Path length | 3859 (251.3) | 3863.8 (243.4) | 0.114 | 845.4 (19.9) | 843.7 (20.2) | 0.001 |
| Mean glucose at 07:00 h (mg/dL) | 120.7 (8.6) | 119.3 (8.8) | <0.001 | — | — | — |

Data in this table are shown as mean (standard deviation). Statistical significance is assessed by paired t-test.

These discussions are consistent with the quartile curves in FIG. 3. Finally, both controllers result in satisfactory glycemic control performance for night time (24:00-06:00 h).

Comparison of performance for the scenario of unannounced meals is provided in FIG. 4 and TABLE III (above). For this scenario, the proposed approach is shown to have much enhanced performance for hyperglycemia control compared with the original zone MPC in terms of percent time in the safe range (72.7% vs. 67.5%; p<0.001), percent time >250 mg/dL (4.5% vs. 6.4%; p<0.001), mean glucose (154.2 mg/dL vs. 160.7 mg/dL; p<0.001). Note, this is achieved without causing the risk of hyperglycemia, which is quantified by percent time <70 mg/dL (0.0% vs. 0.0%) and percent time <54 mg/dL (0.0% vs. 0.0%). The explanation, as observed from FIG. 4, is that due to the glucose state and velocity dependent choice of R and R, the proposed controller encourages reasonably more active insulin infusion when the glucose concentration is rapidly increasing, and is able to safely turn off insulin infusion when the glucose stops to increase or decreases. As indicated above, both controllers lead to satisfactory glycemic control performance for night time (24:00-06:00 h), which is also reflected in the mean glucose concentration values at 07:00 h (119.3 mg/dL vs. 120.7 mg/dL; p<0.001).

Figure 5:
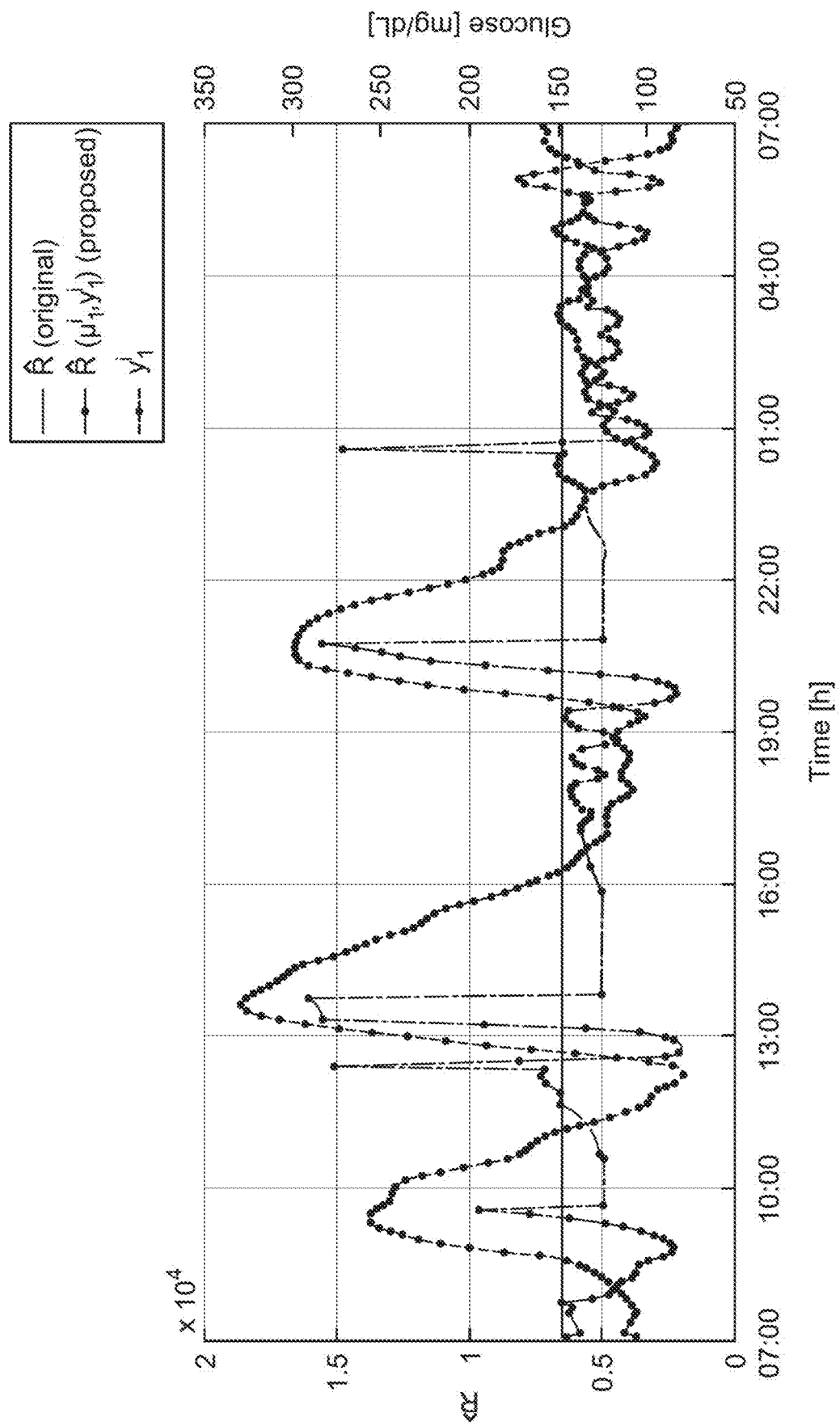
FIG. 5 is a graphical illustration of the adaption of the parameters that control infusion of insulin based on the glucose concentration, in accordance with an embodiment of the present embodiment.

FIG. 5 is a graphical illustration of the adaption of the parameters that control infusion of insulin based on the glucose concentration, in accordance with an embodiment of the present embodiment. The performance improvement of the proposed controller is achieved through the adaptation of control penalty parameters. FIG. 5 specifically plots the trend of $\hat{R}(\mu_1^i, y_1^i)$ of in silico Patient 7 in the first 24 hours (which correspond to 288 controller update instants) with unannounced meals, together with the trend of glucose prediction sequence $\{y_1^i | i=1, \ldots, 288\}$. The superscript i is used to represent the dependence of the variables on time. A comparison with the constant choice of confirms that the proposed parameter adaptation law chooses relatively larger values of $\hat{R}(\cdot, \cdot)$ when the glucose predictions are low, or very high, or decreasing, but allows comparably small values only when the glucose predictions are increasing steeply above the nominal glucose range. This further explains how the proposed adaptive approach manages to alleviate hyperglycemia without causing increased risks of hypoglycemia.

In this work, an adaptive MPC approach is developed for zone MPC of AP based on the predicted glucose state and its velocity. The obtained controller allows appropriate active insulin infusion when blood glucose is rapidly increasing above the nominal value, but cautiously decreases or suspends insulin infusion when glucose velocity is positively small or negative or when the glucose concentration is low. The safety and effectiveness of the proposed method is evaluated on the 10-patient cohort of the FDA-approved UVA/Padova simulator through comparisons with the original zone MPC. Although the approach is developed for the zone MPC, the idea is general enough to be extended to other MPC formulations (e.g., the enhanced MPC with a hybrid exponential and quadratic cost).

FIG. 6 illustrates a process 600 for providing a closed loop adaptive glucose controller. The process is illustrated with reference to components discussed above with respect to FIGS. 1A and 1B. In step 601, the glucose sensor receives data that indicates a concentration of glucose in a bloodstream of the patient. The data received is processed to determine a real time glucose concentration. At step 602, an impeding glycemia protocol is enacted based on the MPC 26 in response to real time glucose concentration. The impeding glycemia protocol includes determining a relationship between predicted glucose concentrations 42, a rate of change of the predicted glucose concentrations, and a set of control parameters that determine insulin doses above and below a patient-specific basal rate. At step 603, the set of control parameters is adapted using the relationships determined. At step 604, a dosage of glucose altering substance to administer is determined 45 using the zone MPC algorithm with the control parameters in real time. At step 605, a command is sent to a pump 28 to administer the dosage of the glucose altering substance.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

We claim:

1. A system for the delivery of a glucose altering substance to a patient, the system comprising:
   a glucose sensor configured to provide a sensor glucose measurement signal representative of a real time glucose concentration;
   an insulin delivery device configured to deliver insulin to a patient in response to control signals; and
   a controller programmed to receive the sensor glucose measurement signal from the glucose sensor, wherein the sensor glucose measurement signal received indicates a concentration of the real time glucose concentration in a bloodstream,
   wherein the controller is further configured to enact an impeding glycemia protocol based on a zone model predictive control (MPC) algorithm in response to the real time glucose concentration, wherein the impeding glycemia protocol comprises determining a relationship between predicted glucose concentrations, a rate of change of the predicted glucose concentrations, and a set of control parameters that determine insulin doses above and below a patient-specific basal rate; wherein the set of control parameters comprise control input glucose velocity penalties; and wherein the control input glucose velocity penalties comprise separate sets of control input glucose velocity penalties for hyperlycemia and hypoglycemia;
   wherein the controller is further configured to adapt the set of control parameters using the relationship determined,
   determine a dosage of the glucose altering substance to administer, using the zone MPC algorithm with the control parameters, in real time, and
   send a command to the insulin delivery device to administer the dosage of the glucose altering substance.

2. The system of claim 1, wherein the controller is further configured to:
   decrease a responsiveness of infusion of the glucose altering substance in response to an increase of glucose state prediction when it is above a normal value to avoid overdosing, and decrease the responsiveness of infusion of the glucose altering substance in response to a decrease of glucose state prediction when the glucose state prediction is below the normal value, and
   decrease the responsiveness of infusion of the glucose altering substance with a decrease of glucose velocity when the glucose velocity is positive.

3. The system of claim 2, wherein the normal value is 110 mg/dL.

4. The system of claim 2, wherein the controller is further configured to:
   decrease insulin infusion to avoid hypoglycemia when the glucose velocity is negative; and
   decrease the responsiveness of infusion of the glucose altering substance in response to an increase of an absolute value of the glucose velocity when the glucose velocity is negative.

5. The system of claim 1, wherein the controller is configured to process the data received at the glucose sensor to determine a set of real time glucose concentrations using a state observer to reduce the effect of noise on when measuring the real time glucose concentration.

6. The system of claim 1, wherein the set of real-time blood glucose measurements are periodically determined by the glucose sensor.

7. The system of claim 1, wherein the MPC comprises the asymmetric cost function of Formula (6):

$$J(\cdot,\cdot) = \sum_{k=1}^{N_p}\left(\check{z}_k^2 + Q(v_k)\hat{z}_k^2 + \hat{D}\hat{v}_k^2\right) + \sum_{k=1}^{N_u-1}\left(\hat{R}(\mu_k, y_k)\hat{u}_k^2 + \check{R}(\mu_k, y_k)\check{u}_k^2\right).$$

8. The system of claim 1, wherein the glucose altering substance comprises at least one of insulin, pramlintide, or glucagon.

9. A method for providing a closed loop adaptive glucose controller, the method comprising:
   receiving data from at least one glucose sensor, wherein the data received indicates a concentration of glucose in a bloodstream;
   processing the data received to determine a real time glucose concentration;
   enacting an impeding glycemia protocol based on a zone model predictive control (MPC) algorithm in response to real time glucose concentration, wherein the impeding glycemia protocol comprises determining a relationship between predicted glucose concentrations, a rate of change of the predicted glucose concentrations, and a set of control parameters that determine insulin doses above and below a patient-specific basal rate; wherein the set of control parameters comprise control input glucose velocity penalties; and wherein the control input glucose velocity penalties comprise separate sets of control input glucose velocity penalties for hyperlycemia and hypoglycemia;
   adapting the set of control parameters using the relationship determined;
   determining a dosage of glucose altering substance to administer using the zone MPC algorithm with the control parameters in real time; and
   sending a command to a pump to administer the dosage of the glucose altering substance.

10. The method of claim 9, wherein the data is processed by a state observer to reduce noise on glucose concentration.

11. The method of claim 9, wherein the glucose altering substance is at least one of insulin, pramlintide, or glucagon.

12. The method of claim 9, wherein the MPC comprises the asymmetric cost function of Formula (6):

$$J(\cdot,\cdot) = \sum_{k=1}^{N_p}\left(\check{z}_k^2 + Q(v_k)\hat{z}_k^2 + \hat{D}\hat{v}_k^2\right) + \sum_{k=1}^{N_u-1}\left(\hat{R}(\mu_k, y_k)\hat{u}_k^2 + \check{R}(\mu_k, y_k)\check{u}_k^2\right).$$

13. The method of claim 12, wherein adapting the set of control parameters comprises decreasing a rate of increase in the dosage of the glucose altering substance when the predicted glucose concentrations is increasing and the real time glucose concentrations is above a normal value.

14. The method of claim 13, wherein adapting the set of control parameters comprises decreasing the rate of increase in the dosage of the glucose altering substance while the set of predicted glucose concentrations is decreasing and the real time glucose concentrations is below the normal value.

* * * * *